(12) United States Patent
Boden, Jr. et al.

(10) Patent No.: US 10,888,692 B2
(45) Date of Patent: Jan. 12, 2021

(54) ELECTRONIC TOOLSET FOR USE WITH MULTIPLE GENERATIONS OF IMPLANTABLE PROGRAMMABLE VALVES WITH OR WITHOUT ORIENTATION FUNCTIONALITY BASED ON A FIXED REFERENCE MAGNET

(71) Applicant: Integra LifeSciences Switzerland Sàrl, Le Locle (CH)

(72) Inventors: Thomas Boden, Jr., Middleboro, MA (US); Patricia D'Aoust, Franklin, MA (US); Alexander Arazawa, Cambridge, MA (US)

(73) Assignee: Integra LifeSciences Switzerland Sàrl, Le Locle (CH)

( * ) Notice: Subject to any disclaimer, the term of this patent is extended or adjusted under 35 U.S.C. 154(b) by 509 days.

(21) Appl. No.: 15/708,600

(22) Filed: Sep. 19, 2017

(65) Prior Publication Data

US 2019/0083765 A1 Mar. 21, 2019

(51) Int. Cl.
*A61M 27/00* (2006.01)
*A61M 39/02* (2006.01)

(52) U.S. Cl.
CPC ... *A61M 27/006* (2013.01); *A61M 2039/0238* (2013.01); *A61M 2205/103* (2013.01);
(Continued)

(58) Field of Classification Search
CPC .......... A61M 27/006; A61M 2205/103; A61M 2205/3317; A61M 27/3331;
(Continued)

(56) References Cited

U.S. PATENT DOCUMENTS 3,902,252 A 9/1975 Farber
4,173,228 A 11/1979 Van Steenwyk et al.
(Continued)

FOREIGN PATENT DOCUMENTS

EP 2 826 517 1/2015

OTHER PUBLICATIONS

Copending, co-owned U.S. Appl. No. 15/708,404, filed Sep. 19, 2017.
(Continued)

*Primary Examiner* — Benjamin J Klein
(74) *Attorney, Agent, or Firm* — Cohen & Hildebrand, PLLC

(57) ABSTRACT

A method for using a universal electronic toolset for indicating and adjusting of an implantable programmable bodily fluid drainage valve regardless of whether the valve includes a fixed reference magnet used to determine an angle of orientation of the implantable programmable bodily fluid drainage valve or not. A magnetic field detection sensor array in an indicator tool of the electronic toolset determines whether the fixed reference magnet is present in the implantable programmable bodily fluid drainage valve. If the presence of the fixed reference magnet is detected then the center and direction of flow of the adjustable valve unit is ascertained via electronic feedback from the electronic toolset; otherwise, the center and direction flow is ascertained via exclusively by manual physical palpation of the valve.

8 Claims, 23 Drawing Sheets

(52) U.S. Cl.
CPC ........... *A61M 2205/3317* (2013.01); *A61M 2205/3331* (2013.01); *A61M 2205/3515* (2013.01); *A61M 2205/50* (2013.01); *A61M 2205/583* (2013.01); *A61M 2205/6054* (2013.01); *A61M 2205/70* (2013.01); *A61M 2209/04* (2013.01)

(58) Field of Classification Search
CPC ...... A61M 2205/3515; A61M 2205/50; A61M 2205/583; A61M 2205/6054; A61M 2205/70; G01R 33/005; G01R 33/0076
See application file for complete search history.

(56) References Cited

U.S. PATENT DOCUMENTS

| | | | |
|---|---|---|---|
| 4,595,390 A | 6/1986 | Hakim et al. |
| 4,608,992 A | 9/1986 | Hakim et al. |
| 4,622,644 A | 11/1986 | Hansen |
| 4,839,809 A | 6/1989 | Leighton et al. |
| 5,309,096 A | 5/1994 | Hoegnelid |
| 5,425,382 A | 6/1995 | Golden et al. |
| 5,438,990 A | 8/1995 | Wahlstrand et al. |
| 5,525,901 A | 6/1996 | Clymer et al. |
| 5,643,194 A | 7/1997 | Negre |
| 5,709,225 A | 1/1998 | Budgifvars et al. |
| 5,758,667 A | 6/1998 | Slettenmark |
| 5,879,297 A | 3/1999 | Haynor et al. |
| 6,101,417 A | 8/2000 | Vogel et al. |
| 6,129,668 A | 10/2000 | Haynor et al. |
| 6,138,681 A | 10/2000 | Chen et al. |
| 6,216,028 B1 | 4/2001 | Haynor et al. |
| 6,242,907 B1 | 6/2001 | Clymer et al. |
| 6,263,230 B1 | 7/2001 | Haynor et al. |
| 6,439,538 B1 | 8/2002 | Ito |
| 6,485,449 B2 | 11/2002 | Ito |
| 6,690,159 B2 | 2/2004 | Burreson et al. |
| 6,702,249 B2 | 3/2004 | Ito |
| 6,707,293 B2 | 3/2004 | Wan et al. |
| 6,850,803 B1 | 2/2005 | Jimenez et al. |
| 6,882,146 B2 | 4/2005 | Maiwald |
| 6,883,241 B2 | 4/2005 | Moskowitz et al. |
| 6,891,367 B2 | 5/2005 | Shinmura et al. |
| 6,937,906 B2 | 8/2005 | Terry et al. |
| 6,951,059 B2 | 10/2005 | Moskowitz et al. |
| 7,126,331 B2 | 10/2006 | Johnson et al. |
| 7,173,419 B1 | 2/2007 | Johnson et al. |
| 7,228,252 B2 | 6/2007 | Alexander et al. |
| 7,301,332 B2 | 11/2007 | Govari et al. |
| 7,334,582 B2 | 2/2008 | Bertrand et al. |
| 7,525,309 B2 | 4/2009 | Sherman et al. |
| 7,753,913 B2 | 7/2010 | Szakelyhidi, Jr. et al. |
| 7,842,004 B2 | 11/2010 | Kassem |
| 7,856,987 B2 | 12/2010 | Bertrand et al. |
| 7,921,571 B2 | 4/2011 | Moureaux et al. |
| 7,945,334 B2 | 5/2011 | Jimenez et al. |
| 8,015,977 B2 | 9/2011 | Bertrand et al. |
| 8,038,641 B2 | 10/2011 | Soares et al. |
| 8,148,978 B2 | 4/2012 | Sherman et al. |
| 8,241,240 B2 | 8/2012 | Murphy |
| 8,257,296 B2 | 9/2012 | Bertrand et al. |
| 8,322,365 B2 | 12/2012 | Wilson et al. |
| 8,398,617 B2 | 3/2013 | Ginggen et al. |
| 8,518,023 B2 | 8/2013 | Roth et al. |
| 8,539,956 B2 | 9/2013 | Bertrand et al. |
| 8,591,499 B2 | 11/2013 | Girardin et al. |
| 8,617,142 B2 | 12/2013 | Wilson et al. |
| 8,622,978 B2 | 1/2014 | Bertrand et al. |
| 8,630,695 B2 | 1/2014 | Negre et al. |
| 8,733,394 B2 | 5/2014 | Negre et al. |
| 8,753,331 B2 | 6/2014 | Murphy |
| 8,862,200 B2 | 10/2014 | Sherman et al. |
| 9,126,010 B2 | 9/2015 | Shah et al. |
| 9,149,615 B2 * | 10/2015 | Wilson ............... A61M 27/006 |
| 9,220,876 B2 | 12/2015 | Girardin et al. |
| 9,242,077 B2 | 1/2016 | Wilson et al. |
| 9,295,826 B2 | 3/2016 | Bertrand et al. |
| 9,364,646 B2 | 6/2016 | Bertrand et al. |
| 9,381,301 B2 | 7/2016 | Lattanzio et al. |
| 9,427,559 B2 | 8/2016 | Shah et al. |
| 9,453,934 B2 | 9/2016 | Hughes |
| 9,585,600 B2 | 3/2017 | Sharonov |
| 2004/0017192 A1 | 1/2004 | Clymer et al. |
| 2004/0055610 A1 | 3/2004 | Forsell |
| 2004/0064030 A1 | 4/2004 | Forsell |
| 2004/0097803 A1 | 5/2004 | Panescu |
| 2004/0250820 A1 | 12/2004 | Forsell |
| 2005/0187509 A1 | 8/2005 | Wolf |
| 2006/0124140 A1 | 6/2006 | Forsell |
| 2007/0276218 A1 | 11/2007 | Yellen |
| 2010/0010338 A1 | 1/2010 | van Dam et al. |
| 2010/0292759 A1 | 11/2010 | Hahn et al. |
| 2011/0031961 A1 | 2/2011 | Durand et al. |
| 2011/0048539 A1 * | 3/2011 | Negre ............... A61M 27/006 137/1 |
| 2011/0105991 A1 * | 5/2011 | Roth ................. F16K 37/0041 604/9 |
| 2012/0041297 A1 | 2/2012 | McGary |
| 2012/0302938 A1 | 11/2012 | Browd et al. |
| 2013/0197422 A1 | 8/2013 | Browd et al. |
| 2014/0336560 A1 | 11/2014 | Hakim |
| 2015/0196742 A1 | 7/2015 | Browd et al. |
| 2016/0089519 A1 | 3/2016 | Bittenson |
| 2016/0166813 A1 | 6/2016 | Bertrand et al. |
| 2016/0184563 A1 | 6/2016 | Bertrand et al. |
| 2016/0279396 A1 | 9/2016 | Bertrand et al. |
| 2017/0095650 A1 | 4/2017 | Wilson |
| 2017/0209056 A1 | 7/2017 | Browd et al. |
| 2018/0001064 A1 | 1/2018 | Pfleiderer et al. |
| 2018/0015266 A1 * | 1/2018 | Amery .................... H03F 1/52 |
| 2018/0126147 A1 | 5/2018 | Hakim |
| 2018/0184943 A1 | 7/2018 | Boden |
| 2018/0243542 A1 | 8/2018 | Pfleiderer et al. |

OTHER PUBLICATIONS

Copending, co-owned U.S. Appl. No. 15/708,496, filed Sep. 19, 2017.

Copending, co-owned U.S. Appl. No. 15/708,549, filed Sep. 19, 2017.

* cited by examiner

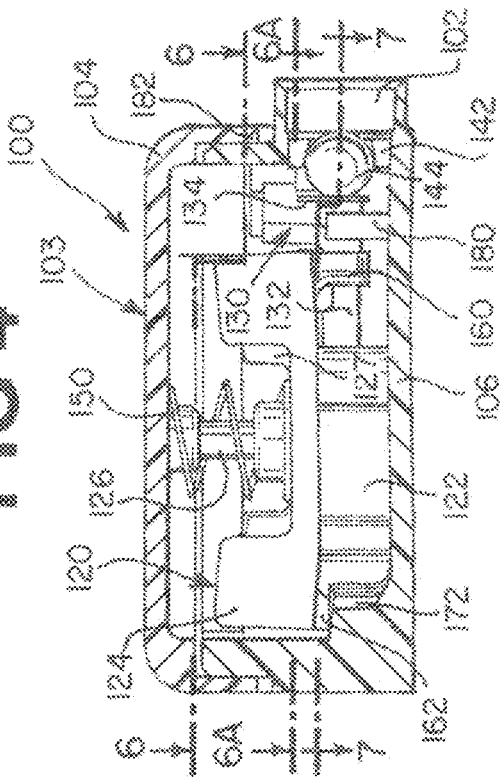
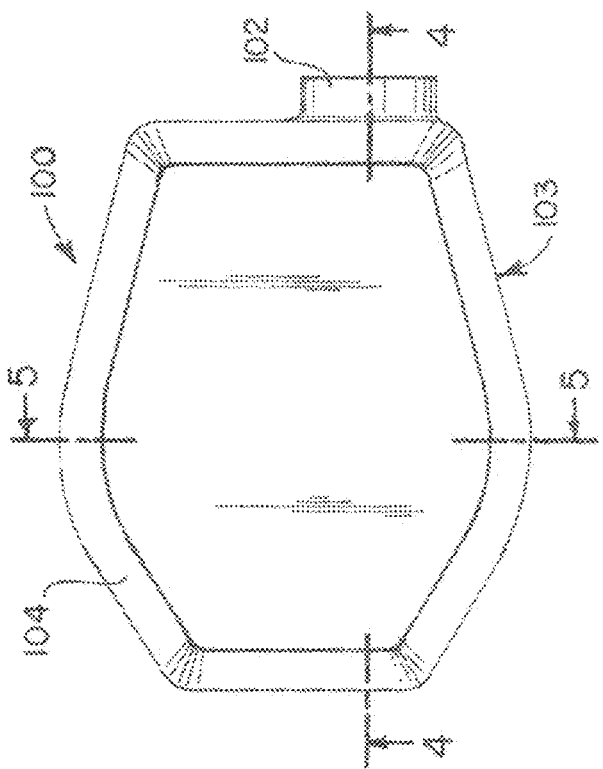

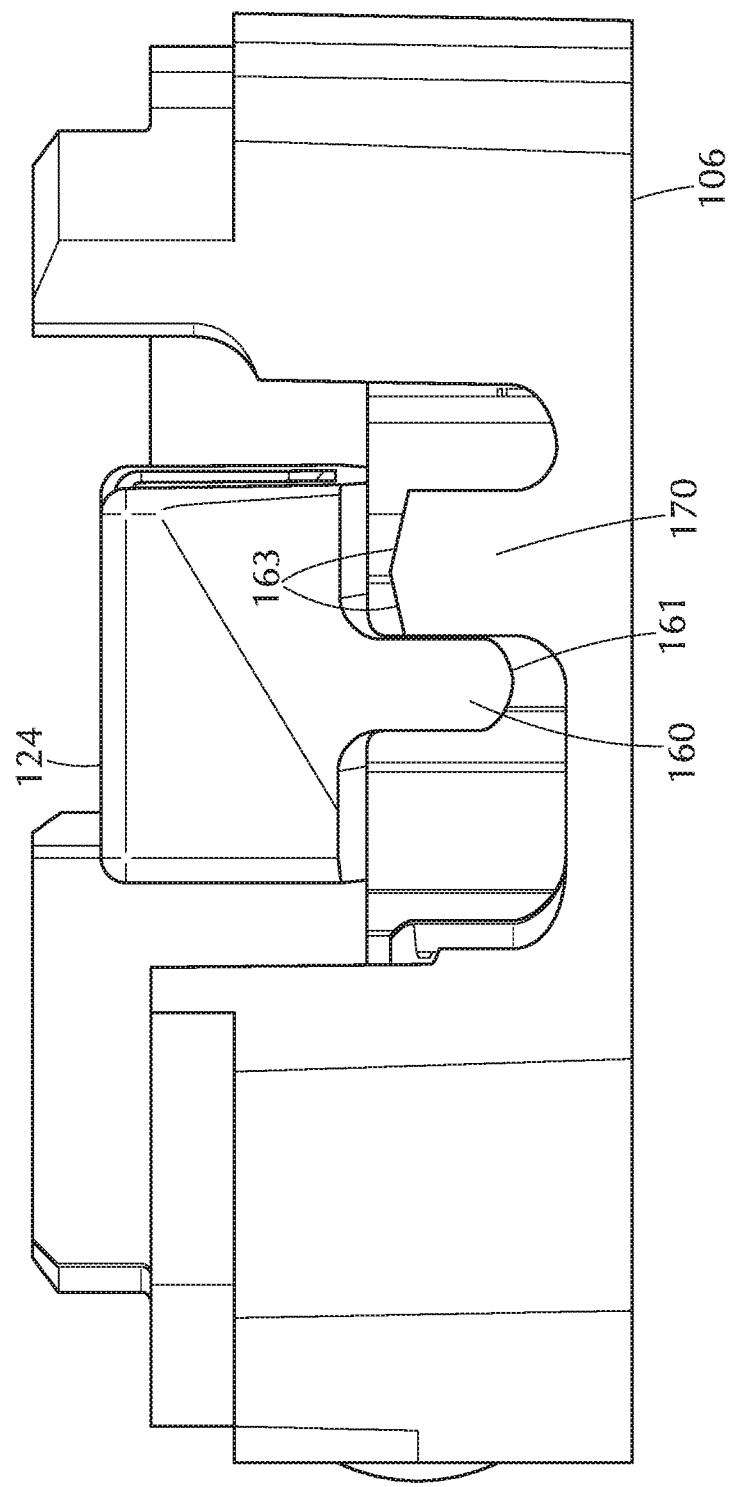

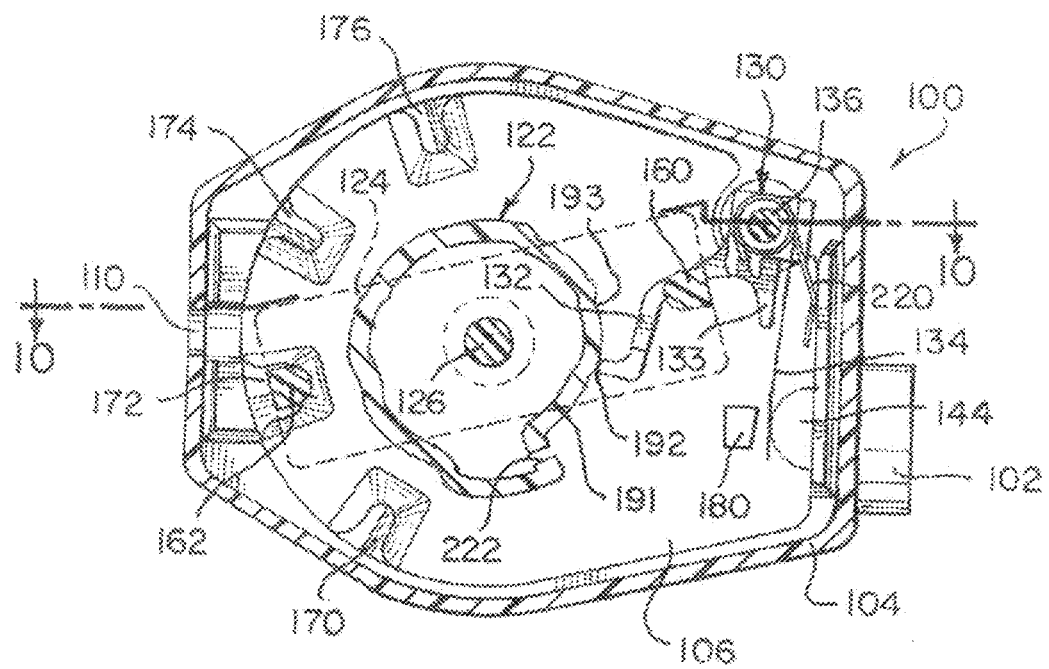
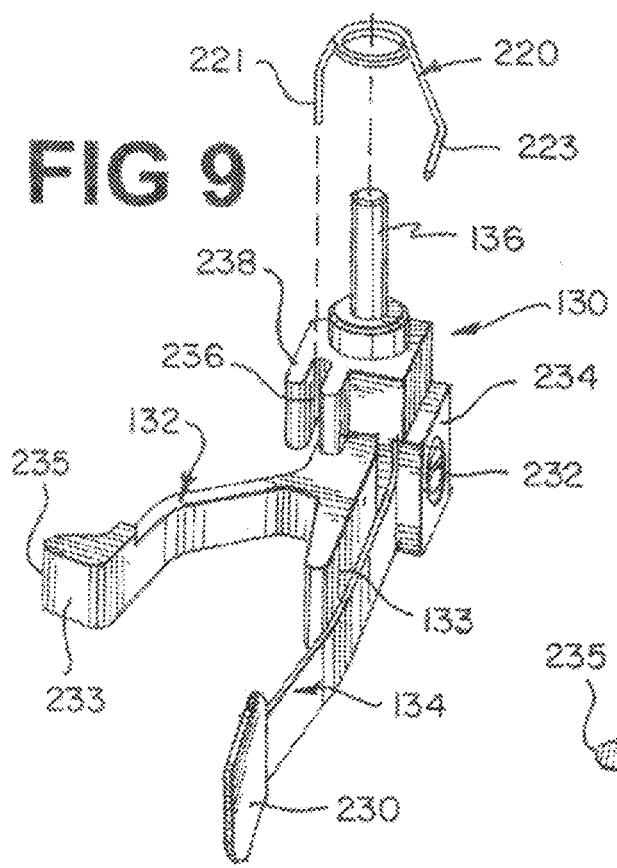
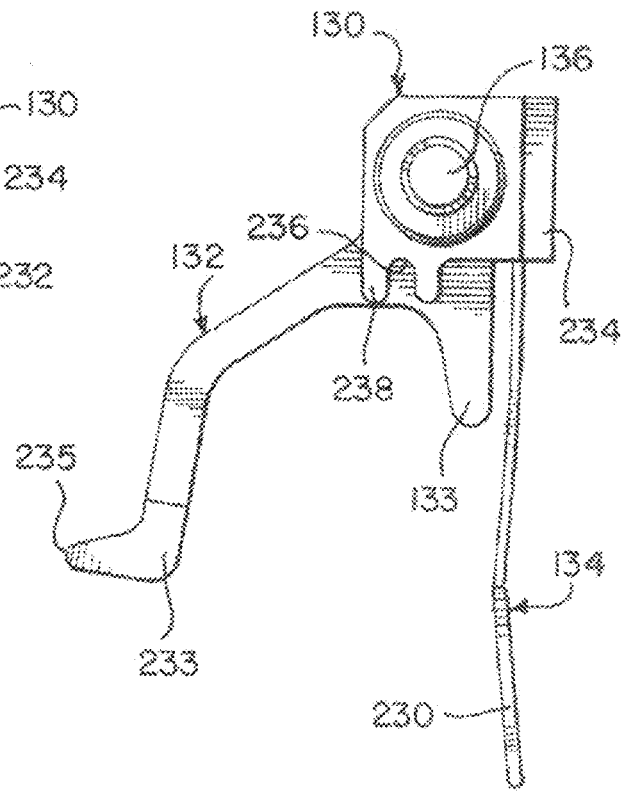

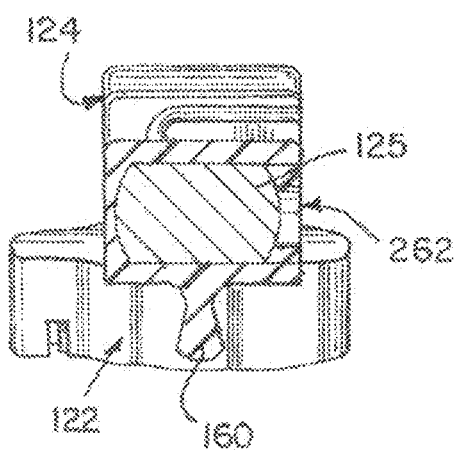

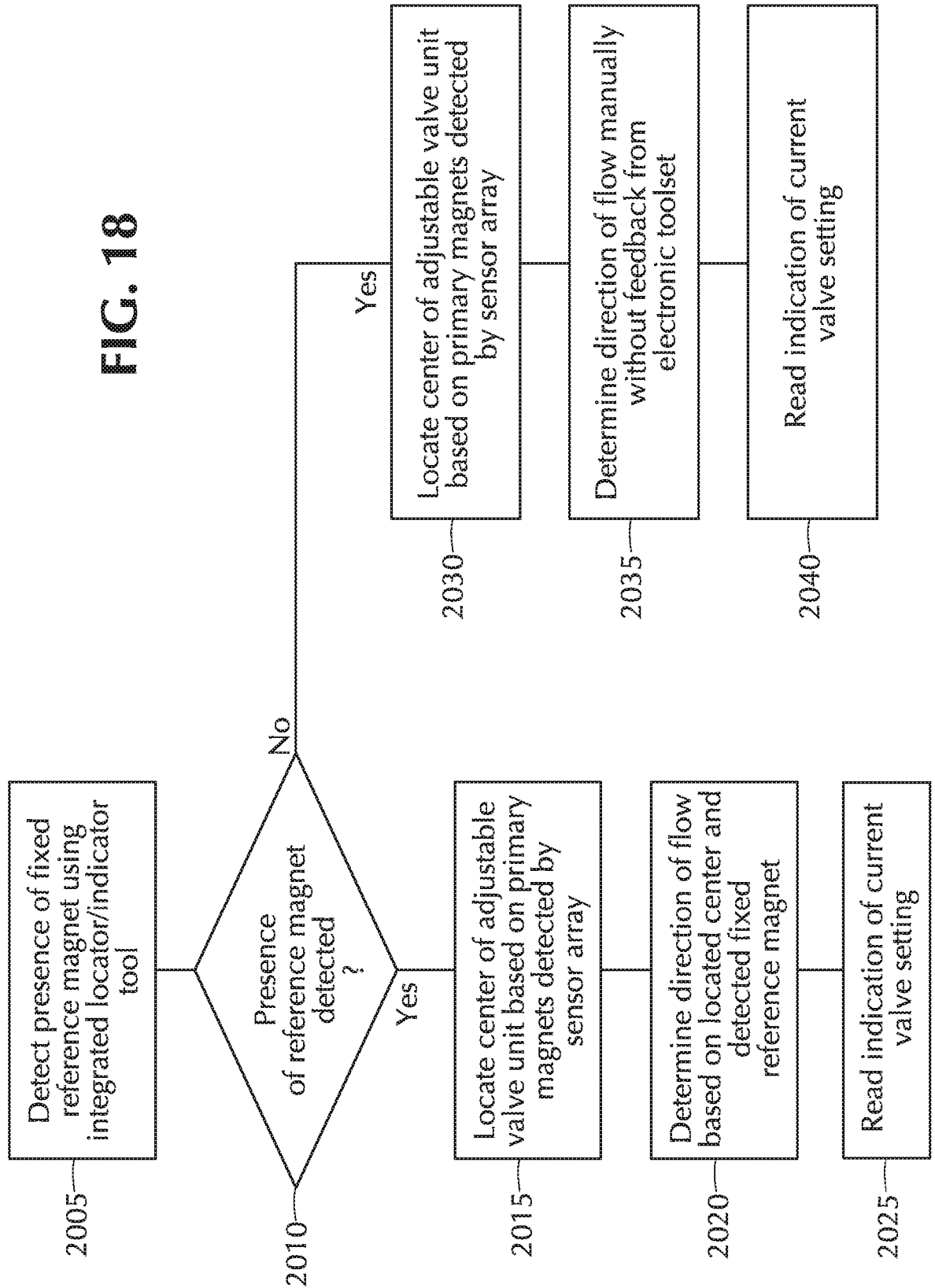

ELECTRONIC TOOLSET FOR USE WITH MULTIPLE GENERATIONS OF IMPLANTABLE PROGRAMMABLE VALVES WITH OR WITHOUT ORIENTATION FUNCTIONALITY BASED ON A FIXED REFERENCE MAGNET

BACKGROUND OF THE INVENTION

Field of the Invention

The present invention relates to a system and method for an implantable drainage valve for drainage of a bodily fluid (e.g., cerebrospinal fluid). In particular, the present inventive system and method is directed to an electronic toolset for indicating and adjusting with automatic switching between multiple generations of implantable bodily fluid drainage valves with and without orientation functionality.

Description of Related Art

Hydrocephalus is the accumulation of cerebrospinal fluid in the brain, resulting from increased production, or more commonly, pathway obstruction or decreased absorption of the fluid. Cerebrospinal fluid (CSF) shunts have been used for decades for the treatment of hydrocephalus. A CSF shunt involves establishing an accessory pathway for the movement of CSF to bypass an obstruction of the natural pathways.

The shunt is positioned to enable the CSF to be drained from the cerebral ventricles or sub-arachnoid spaces into another absorption site (e.g., the right atrium of the heart or the peritoneal cavity) through a system of small catheters. A regulatory device, such as a valve, may be inserted into the pathway of the catheters. In general, the valve keeps the CSF flowing away from the brain and moderates the pressure or flow rate. The drainage system using catheters and valves enables the excess CSF within the brain to be evacuated and, thereby, the pressure within the cranium to be reduced.

Some implantable valves are fixed pressure valves (i.e., monopressure valves) while others have adjustable or programmable settings. Programmable or adjustable implantable valves are desirable in that the valve pressure setting may be varied non-invasively via an external control device over the course of treatment without requiring explantation. One such conventional adjustable or programmable implantable valve using magnets is the CODMAN® HAKIM® Programmable Valve (CHPV), as disclosed in U.S. Pat. No. 4,595,390, which is assigned to DePuy Orthopedics, a J&J company related to that of the present assignee, and herein incorporated by reference in its entirety. Another programmable implantable drainage valve is the CODMAN® CERTAS® or CERTAS® Plus Programmable Valve, as disclosed in U.S. Pat. No. 8,322,365, also assigned to DePuy Orthopedics, a J&J company related to that of the present assignee, and which is herein incorporated by reference in its entirety. Medtronic also has a programmable implantable shunt valve Strata® controlled using magnets. The pressure setting in these aforementioned conventional programmable implantable valves may be non-invasively adjusted post implantation in the body using a rotating construct or rotor with a pair of magnets.

Each programmable implantable valve is controlled using an associated external toolset comprising one or more devices used to locate the valve, read the current valve setting and adjust the valve setting. With each improved generation or version of the programmable implantable valve an associated toolset may be required. However, often the electronic toolset used for indicating and adjusting the latest generation of the programmable implantable valve is inoperable on an earlier generation or version of the programmable implantable valve. As a result, medical personnel are required to store multiple versions of the electronic toolset (i.e., not just the latest improved version, but previous versions also) as well as properly use each electronic toolset only with the applicable programmable implantable valve. Furthermore, it is not always clear from the patient records or x-ray identification, what generation of valve is implanted in the patient based on which the appropriate toolset is selected.

It is therefore desirable to develop a universal or interchangeable electronic toolset for use in indicating and adjusting multiple generations or versions of programmable implantable valves that can automatically switch without additional input from the clinician between generations of valves with or without orientation functionality.

SUMMARY OF THE INVENTION

An aspect of the present invention is directed to a universal or interchangeable electronic toolset for use in indicating and adjusting multiple generations or versions of programmable implantable valves that can automatically switch without additional input from the clinician between generations of valves with or without orientation functionality.

Another aspect of the present invention relates to a method for using a universal electronic toolset for indicating and adjusting of an implantable programmable bodily fluid drainage valve whether the implantable programmable bodily fluid drainage valve includes a fixed reference magnet used to determine an angle of orientation of the implantable programmable bodily fluid drainage valve or not, wherein the implantable programmable bodily fluid drainage valve includes an adjustable valve unit having a pair of primary magnetic elements. Using a magnetic field detection sensor array in an indicator tool of the electronic toolset it is determined whether the fixed reference magnet is present in the implantable programmable bodily fluid drainage valve. If the presence of the fixed reference magnet in the implantable bodily fluid drainage valve is detected then: a center of the adjustable valve unit is located using the indicator tool of the electronic toolset; a direction of flow of the adjustable valve unit is ascertained based exclusively on electronic feedback provided by the indicator tool of the electronic toolset, without requiring manual physical palpation; the indicator tool of the electronic toolset is aligned with the located center and the direction of flow of the adjustable valve unit; and a current valve setting is read using the indicator tool of the electronic toolset. Otherwise, if the presence of the fixed reference magnet is in the implantable programmable bodily fluid drainage valve is not detected then: the center of the adjustable valve unit is located using the indicator tool of the electronic toolset; the direction of flow of the adjustable valve unit is established exclusively by manual physical palpation, without electronic feedback from the indicator tool of the electronic toolset; the indicator tool of the electronic toolset is aligned with the located center and the direction of flow of the adjustable valve unit; and the current valve setting is read using the indicator tool of the electronic toolset.

Yet another aspect of the present invention is directed to an implantable programmable bodily fluid drainage valve system including an implantable programmable bodily fluid drainage valve having an adjustable valve unit including a pair of primary magnetic elements for programming the implantable programmable bodily fluid drainage valve to a desired valve setting. The system also includes a universal electronic toolset for indicating and adjusting the implantable programmable bodily fluid drainage valve. In that, the universal electronic toolset includes an indicator tool having a magnetic field detection sensor array for: (i) detecting the pair of primary magnetic elements; and (ii) determining the presence or absence of a fixed reference magnet in the implantable programmable bodily fluid drainage valve. Circuitry is provided for determining a center of the adjustable valve unit based on the detected pair of primary magnetic elements. Such circuitry determines exclusively by electronic feedback from the toolset an angular orientation of the implantable programmable bodily fluid drainage valve, when the fixed reference magnet is present; whereas the circuitry generates on a display of the implantable programmable bodily fluid drainage valve steps for determining exclusively by manual physical palpation the angular orientation and/or center of the implantable programmable bodily fluid drainage valve, when the fixed reference magnet is absent.

BRIEF DESCRIPTION OF THE DRAWING

The foregoing and other features of the present invention will be more readily apparent from the following detailed description and drawings of illustrative of the invention wherein like reference numbers refer to similar elements throughout the several views and in which:

FIG. 3 is a top view of the adjustable valve unit of FIG. 2;

FIG. 4 is a side cross-sectional view of the adjustable valve unit of FIG. 3 along lines 4-4;

FIG. 4A is a side view of a single rotor tooth in engagement with a single lock stop;

FIG. 8 is a cross-sectional view of the adjustable valve unit of FIG. 7 showing the transition to a different pressure setting;

FIG. 9 is a perspective view of the spring arm unit with optional torsion spring;

FIG. 9A is a top plan view of the element of FIG. 9;

FIG. 13A is a partial cross-sectional view along lines 13A-13A of FIG. 13;

FIG. 18 is a flow chart of the method for ascertain whether the implanted valve is a current valve with orientation functionality (i.e., employs a fixed reference magnet) in accordance with the present invention or a previous version of the implanted valve without orientation functionality (i.e., does not employ a fixed reference magnet).

DETAILED DESCRIPTION OF THE INVENTION

Figure 1:
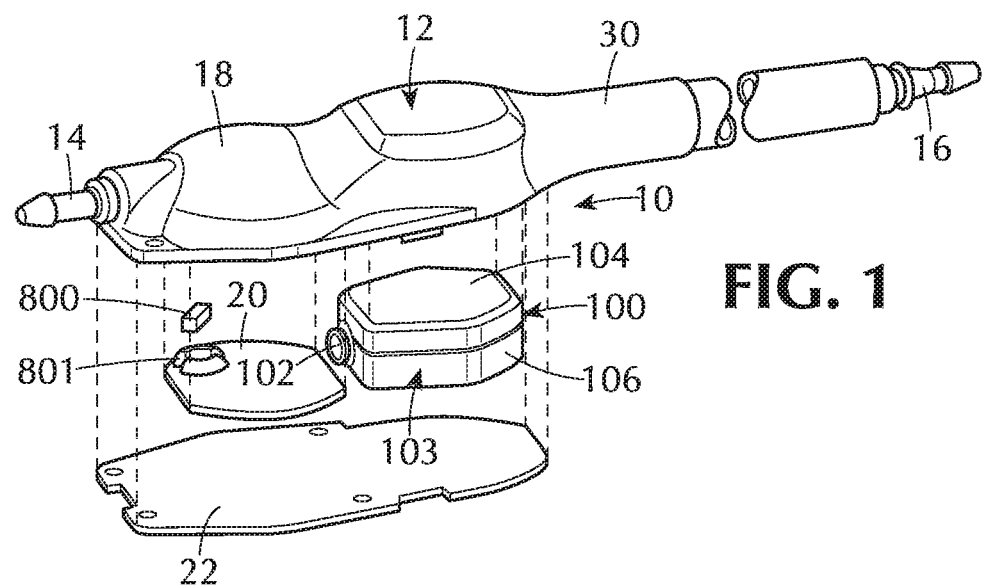
FIG. 1 is a schematic perspective exploded view of a programmable implantable valve device having a fixed reference magnet in addition to the rotational primary magnets associated with the adjustable valve unit.

FIG. 1 illustrates a programmable shunt valve device 10 having a shunt housing 12, preferably formed of a translucent material such as silicone, with proximal connector 14 and distal connector 16. A ventricular catheter or other proximal catheter is connectable to connector 14 to bring fluid into shunt housing 12. Fluid passes into sampling or pumping chamber 18 and then through a valve mechanism in inlet 102 into adjustable valve unit 100, which is shown and described in more detail below in relation to FIGS. 2-13A. Adjustable valve unit 100, FIG. 1, includes a casing 103 formed as upper casing 104 and lower casing 106 which are joined by sonic welding in this construction. A needle guard 20, preferably formed of a rigid polymeric material, and lower casing 106 are secured within housing 12 by a backing plate 22, preferably formed of silicone reinforced with a polymeric mesh, which is bonded to housing 12 by a medical grade epoxy. A fixed reference magnet 800, as described in detail further below, is preferably seated in a bump or projection 801 on the needle guard 20.

When fluid pressure at inlet 102 exceeds a selected pressure setting within adjustable valve unit 100, fluid is admitted past a valve mechanism and then flows through valve unit outlet 110 into passage 30 of housing 12. Ultimately, fluid exits from housing 12 through distal connector 16 into a peritoneal catheter or other distal catheter.

Figure 2:
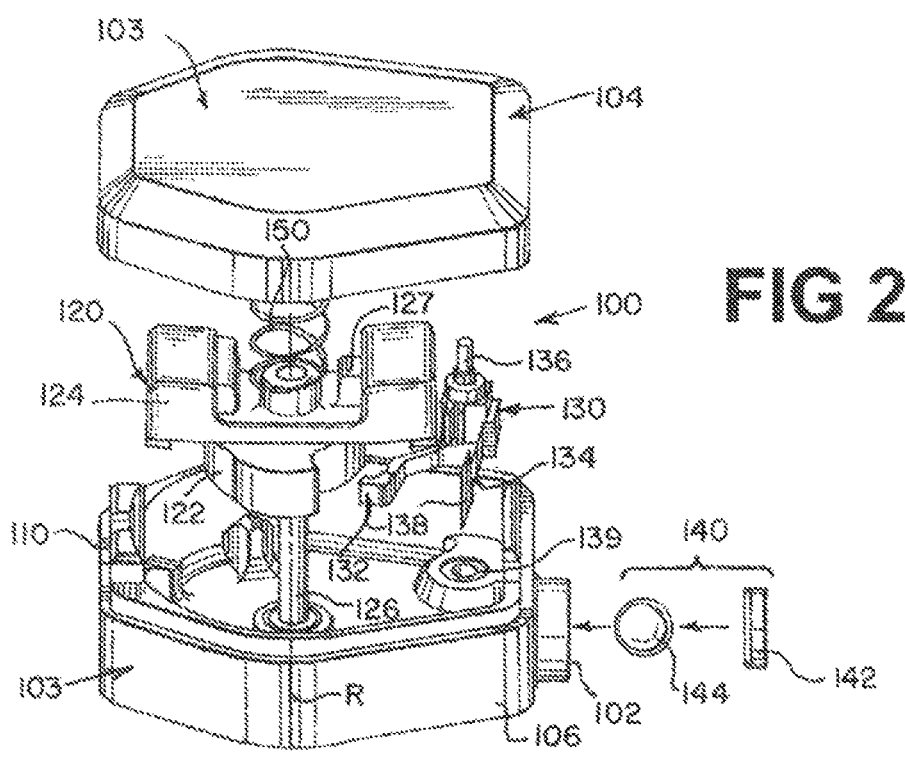
FIG. 2 is an exploded perspective view of the adjustable valve unit of FIG. 1.

Adjustable valve unit 100, FIG. 2, includes a rotor 120, spring arm unit 130, valve mechanism 140, and a rotor retention spring 150. Rotor 120, also referred to as a rotating construct, is formed of a lower cam structure 122 having a plurality of radially flat cam surfaces, as shown and described in more detail below, and an upper, magnet housing 124 carrying magnetic elements 123 and 125, N and S pole magnets, respectively. Housing 124 also defines a finger 127 which engages a stop in upper casing 104 when rotor 120 is moved to an unconstrained condition as described below. Rotor 120 rotates about axle 126 which defines a substantially fixed axis of rotation R at a first location in casing 103.

Preferably, rotor 120 is also capable of moving along the axis of rotation, in a translational motion, to an unconstrained condition when an adjustment tool from an electronic toolset is applied to it, as described in more detail below. Retention spring 150 biases rotor 120 to a downward, normally constrained condition. Preferably, spring 150 is a coil spring having sufficient bias to resist the effect of gravity, regardless of the position of the adjustable valve unit 100, and to resist magnetic or ferrous objects, such as magnets in an integrated locator/indicator tool from the electronic toolset, as described in more detail below. However, spring 150 is insufficient to resist the effects of the adjustment tool, also described below. Lower cam section 122 has a sufficient height to ensure that cam follower 132 remains in contact with a cam surface in both the constrained and unconstrained conditions.

Spring arm unit 130 includes cam follower 132, a resilient spring element 134 as well as upper and lower axles 136, 138 at a second location in casing 103. Axle 138 turns about a bearing 139 formed of a relatively low-friction, relatively hard material such as synthetic ruby. It is desirable for casing 103, rotor 120 and spring arm unit 130 to be formed of polyethersulfone, while all spring components are formed of medical grade non-ferromagnetic stainless steel.

Valve mechanism 140 includes seat 142 and movable valve member 144. Preferably, seat 142 and valve member 144, such as a ball, are formed of the same non-ferromagnetic material such as synthetic ruby. In other constructions, the movable valve member 144 may be a disc, a cone, or other type of plug. A spherical ball is currently preferred as the moveable valve member because that shape enables tight, precise tolerances, assembly and control relative to the valve seat. Also, the position of the seat within a port can be adjusted during assembly of the valve unit to alter the actual performance value achieved at each setting, using a force versus displacement relationship. First, a mandrel checks the position of the ball, and the seat is inserted to an estimated desirable location within the port. Ball displacement is tested at one or more settings to confirm that desired performance will be achieved.

Figure 5:
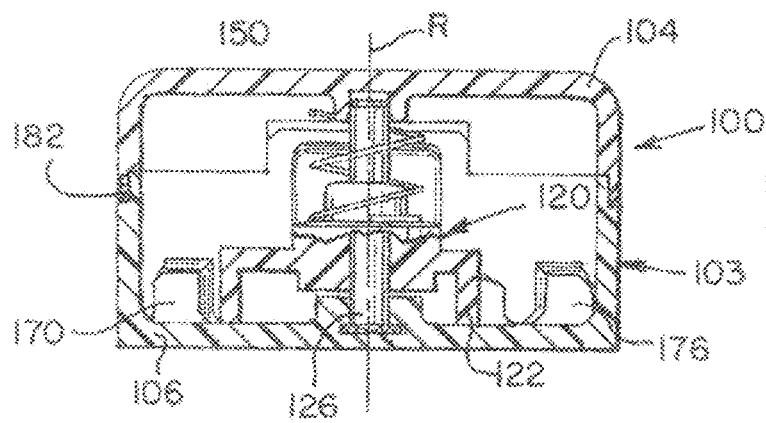
FIG. 5 is a cross-sectional view of the adjustable valve unit of FIG. 3 along lines 5-5.

Adjustable valve unit 100 is shown assembled in FIGS. 3-5 and positioned at a second pressure setting, as described in more detail below. Rotor housing 124 carries downwardly projecting teeth 160 and 162 with cooperate with four lock stops 170, 172, 174, 176 projecting upwardly from lower casing 106 in this construction. Lock stop 172 is shown in partial cross-section in FIG. 4 and lock stops 170 and 176 are visible in FIG. 5. Preferably, the lower surfaces 161 of rotor teeth 160 and 162 are rounded and the upper surfaces of casing lock stops 170, 172, 174 and 176 each have a plurality of facets 163 to create a chisel-like, lead-in topography which encourages the rotor teeth to return to a constrained position, as illustrated in the side view in FIG. 4A. However, the vertical surfaces of the rotor teeth 160, 162 and of lock stops 170-176 abut when engaged and do not "lead out", that is, relative translational movement is discouraged, once again illustrated in FIG. 4A. Pure vertical lift must therefore be provided by an adjustment tool, as described in more detail below, to overcome the rotor teeth-to-lock stop abutment and change the performance setting.

A limiter 180, FIG. 4, restricts travel of spring 134 away from seat 142 so that ball 144 does not become misaligned or dislodged relative to seat 142. A gasket 182 of epoxy is shown in FIGS. 4 & 5 as an optional, redundant seal between upper casing 104 and lower casing 106 in this construction.

Figure 6:
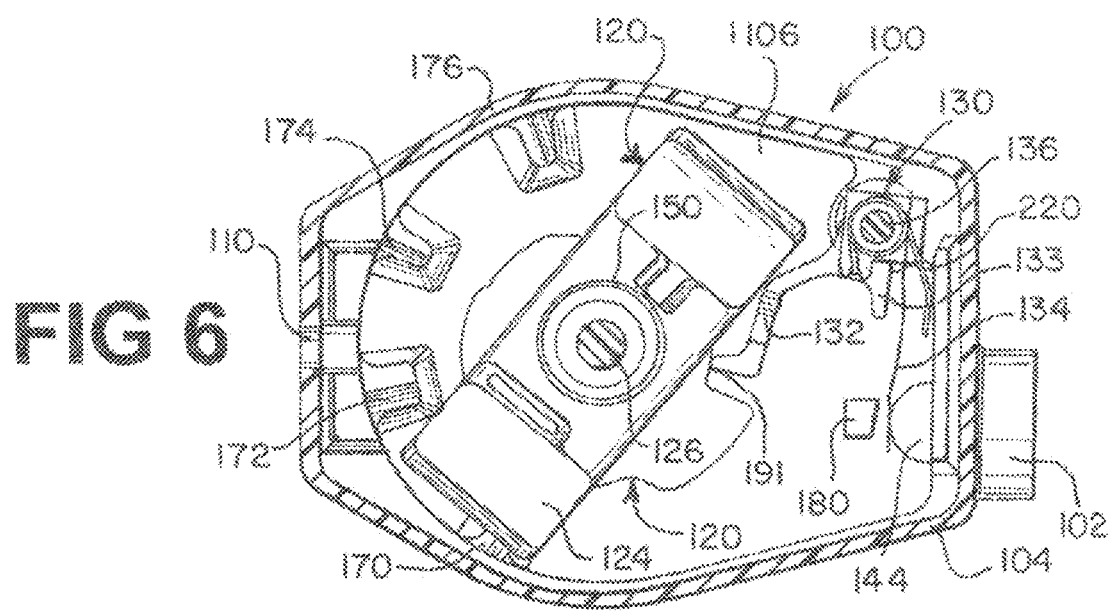
FIG. 6 is a partial cross-sectional view of the adjustable valve unit of FIG. 4 approximately along lines 6-6 at a first pressure setting.
Figure 6A:
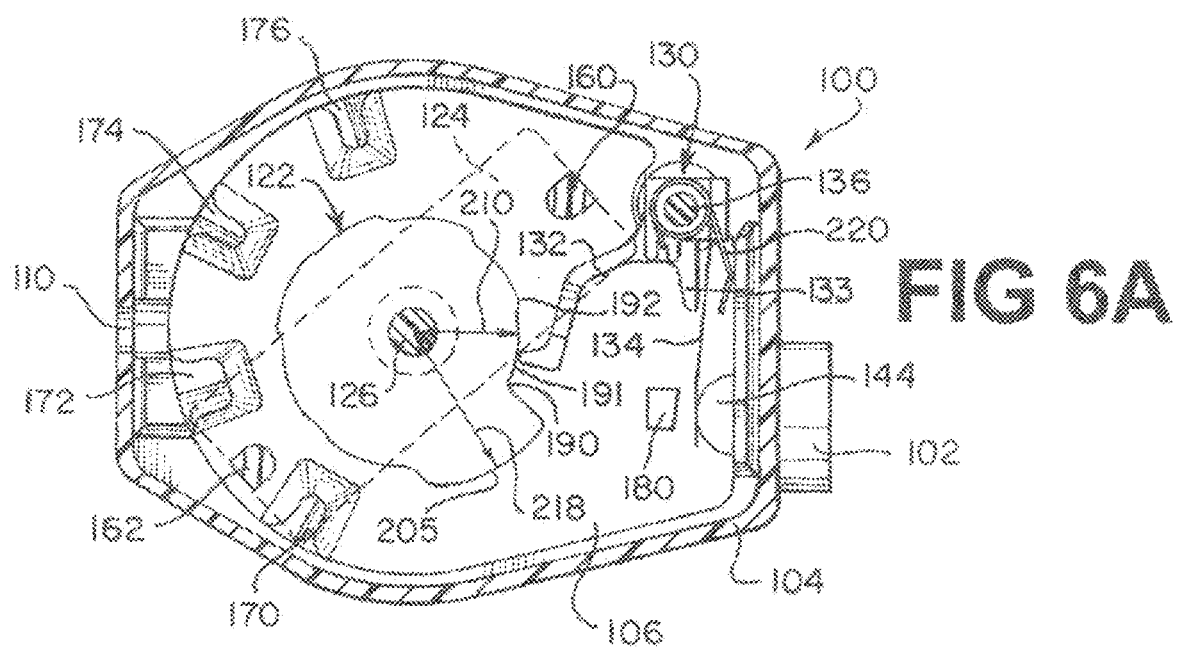
FIG. 6A is a deeper cross-sectional view of the adjustable valve unit of FIG. 4 approximately along lines 6A-6A at a first pressure setting.
Figure 7:
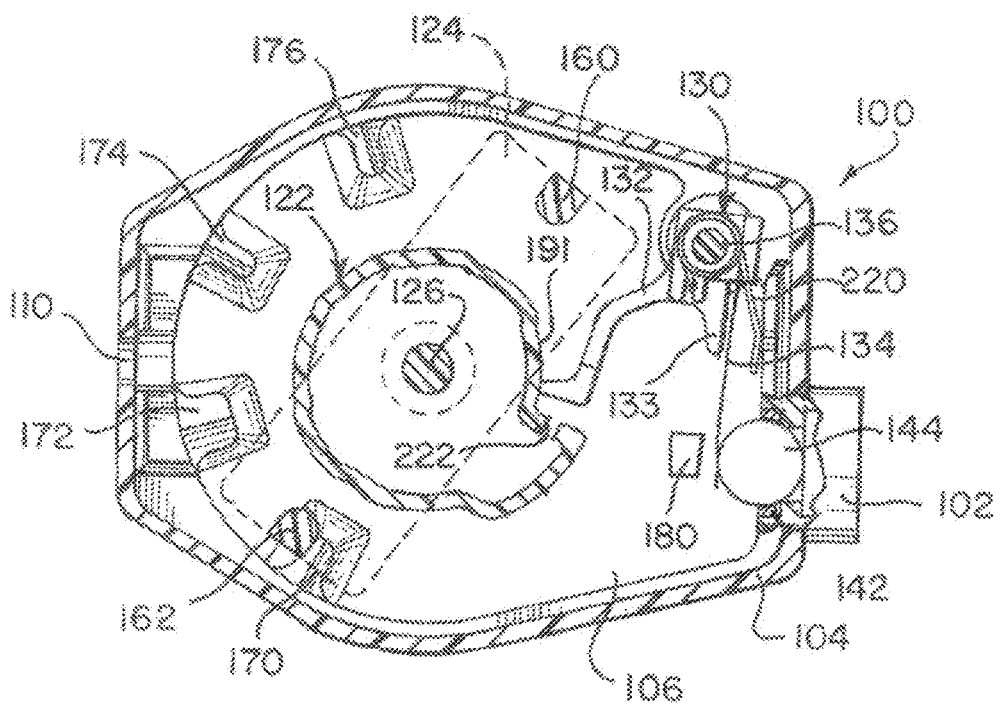
FIG. 7 is a deeper cross-sectional view of the adjustable valve unit of FIG. 4 along lines 7-7.

The operation of adjustable valve unit 100 is illustrated in FIGS. 6-8 with identical reference numerals identifying identical components and features. Not all such components and features are labelled in each drawing for the sake of visual clarity. FIGS. 6 & 6A show different levels of top partial cross-sectional views for adjustable valve unit 100 at a first pressure setting. Cam follower 132 slidably contacts only a first cam surface 191, which has an arc length bounded by points 190 and 192, because rotor housing tooth 162 is captured between casing lock stops 170 and 172 in the normal, constrained condition. First cam surface 191 has a first, preferably shortest radial distance 210 relative to the axis of rotation of rotor 120. By comparison, outermost cam surface 205 has a greatest radial distance 218. An optional torsion spring 220 is shown in greater detail in FIG. 9.

When rotor 120 is translated upwardly by magnets using an adjustment tool rotor tooth 162 is lifted so that subsequent clockwise or counter-clockwise rotation of the adjustment tool rotates rotor tooth 162 up and over casing lock stop 172. After the adjustment tool is removed and when the second pressure setting has been selected as shown in FIG. 6B, rotor 120 is biased downwardly by spring 150, FIGS. 2, 4 & 5.

Figure 6B:
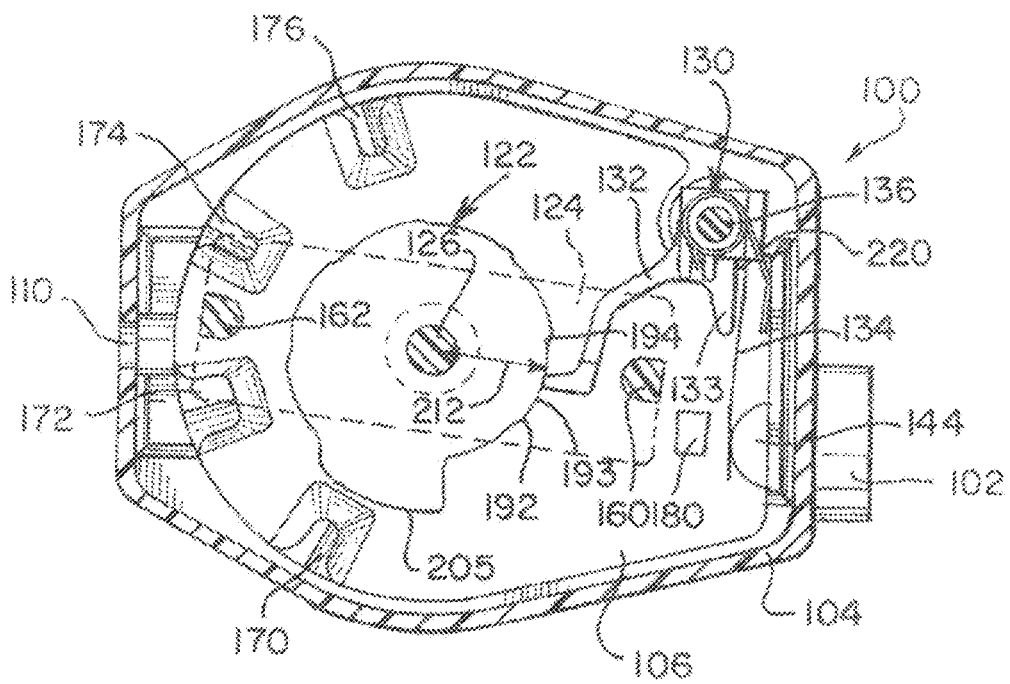
FIGS. 6B-6H are partial cross-sectional view of the adjustable valve unit of FIG. 4 at different, successive pressure settings.

Rotor tooth 160 is illustrated as not being in contact with any stop in FIGS. 4 & 6B, for example, because in the constrained condition rotor tooth 162 is now captured between a pair of adjacent lock stops 172 and 174, FIG. 6B, which is sufficient to prevent rotation of rotor 120 relative to the cam follower 132 beyond points 192 and 194 on the cam structure of rotor 120. Points 192 and 194 represent a second arc length for second cam surface 193. Surface 193 is at a second radial distance 212 which is greater than distance 210 and is less than distance 218, FIGS. 6A & 6H. The arc length of second cam surface 193, FIG. 6B, can be the same or different than the arc length of first cam surface 191 but, preferably, is substantially the same length.

The outward radial motion of cam follower 132 as it slidably travels from first cam surface 191, FIG. 6A, to second cam surface 193, FIG. 6B, increases the biasing force by valve spring 134 on ball 144 as increased torque is applied by cam follower 132 to the remainder of spring arm unit 130. Improved precision in pressure control is achieved by having a stiff cam follower 132 in contact with the selected cam surface and a flexible element, spring 134, in contact with the valve ball 144. The enhanced result is opening of the ball 144 from the valve seat 142 by requiring only the resilient spring element 134 to bend, which provides a constant spring force to the ball 144. The opening pressure, and overall valve performance, is not reliant on axial pivoting of the spring arm unit 130.

Figure 6C:
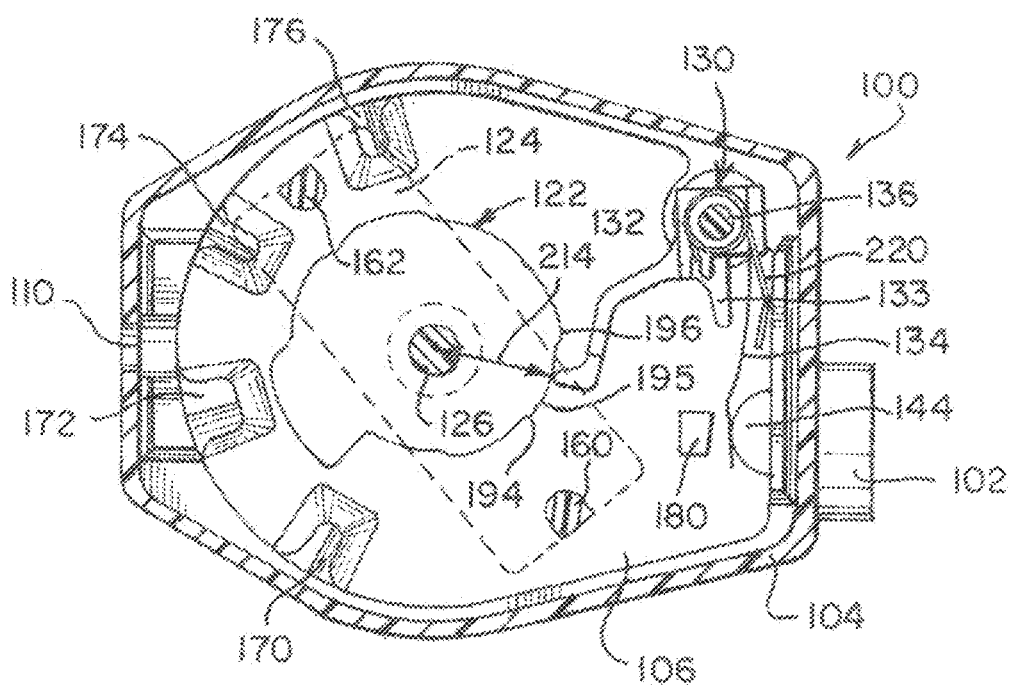
Figure 6D:
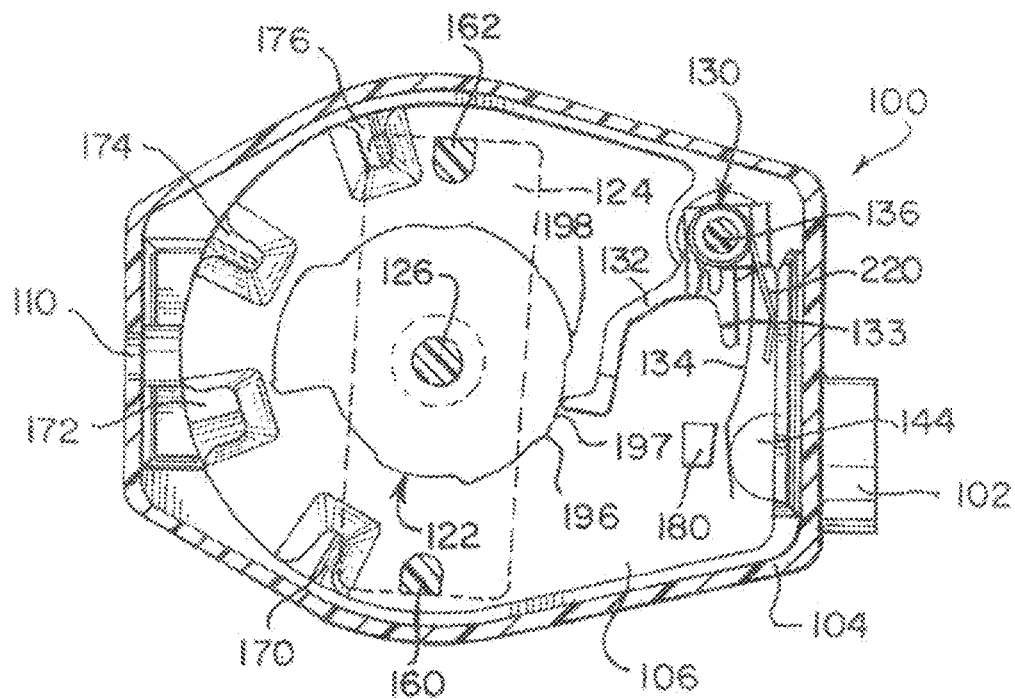

A third opening pressure setting is shown in FIG. 6C with rotor tooth 162 positioned between casing stops 174 and 176 such that cam follower 132 experiences only third cam surface 195 between points 194 and 196 at a third radial distance 214. To achieve a fourth pressure setting, FIG. 6D, both rotor teeth 160 and 162 are utilized relative to casing stops 170 and 176, respectively. Cam follower 132 is restricted thereby to fourth cam surface 197 between points 196 and 198.

Figure 6E:
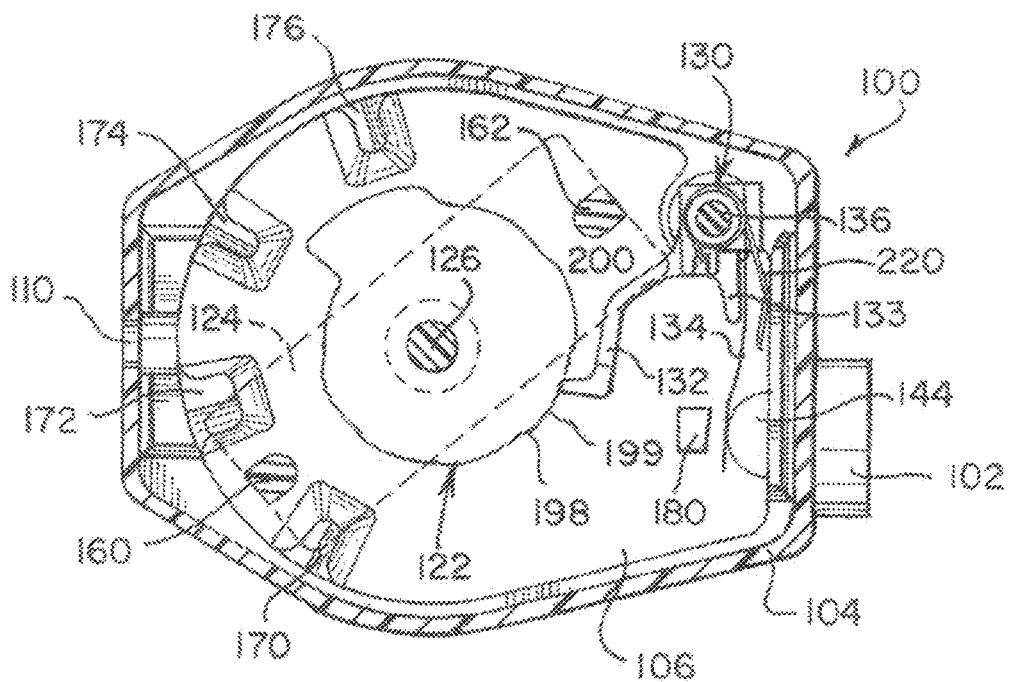
Figure 6F:
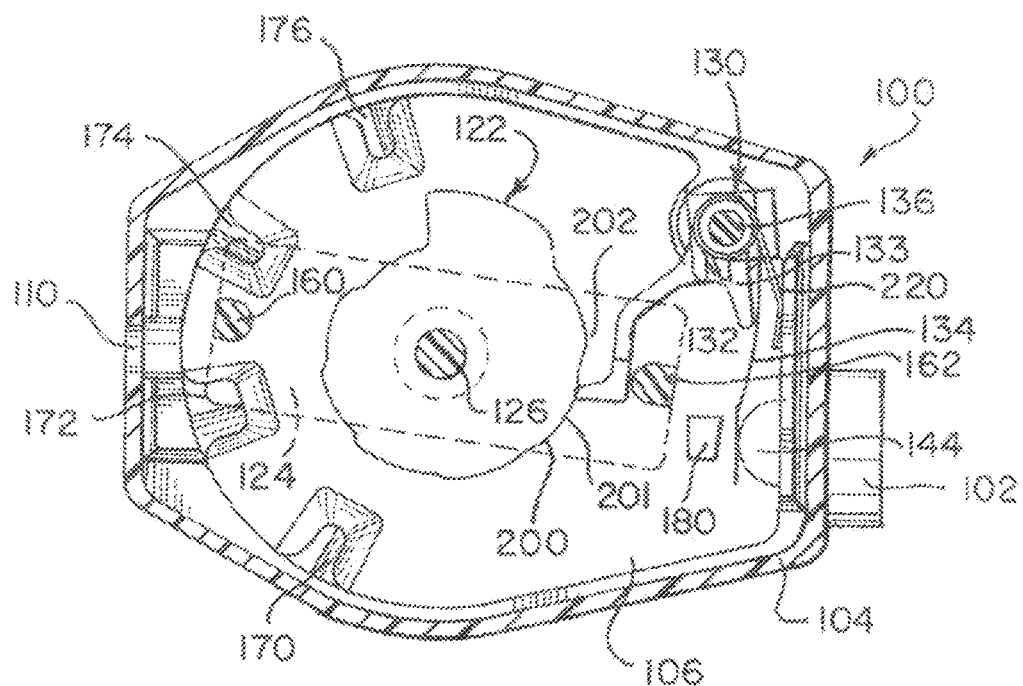
Figure 6G:
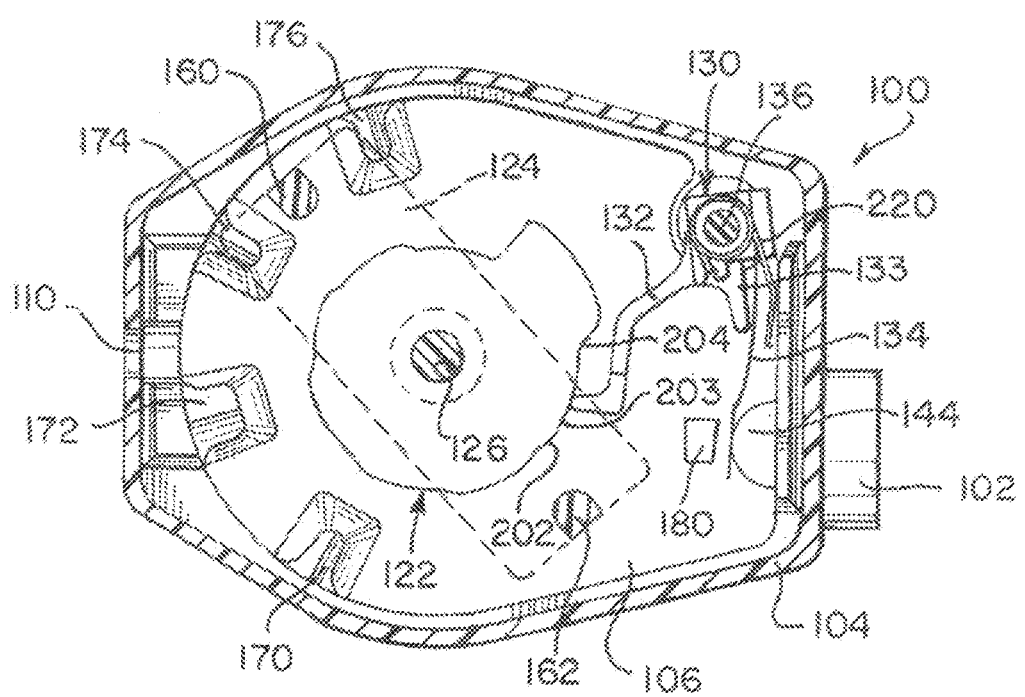

Fifth through seventh pressure settings are illustrated in FIGS. 6E-6G as rotor tooth 160 is successively captured between casing adjacent lock stop pairs 170-172, 172-174, and 174-176, respectively. Cam follower 132 is restricted thereby to fifth cam surface 199 between points 198 and 200, FIG. 6E, sixth cam surface 201 between points 200 and 202, FIG. 6F, and seventh cam surface 203 between points 202 and 204, FIG. 6G.

Preferred opening pressure settings currently range from approximately 30 mm to 210 mm water (294 Pa to 2,059 Pa) in seven increments of 30 mm (294 Pa), with a final, "virtual off" setting described in more detail below. Preferably, each valve unit is calibrated and tested at the time of manufacture at one or more flow rates. Actual opening pressure for each setting tends to vary according to flow rate, typically measured in milliliters per hour. Also, when tested with a 120 cm long distal catheter having an inner diameter of 1 mm, the average opening pressure typically will increase by 9 mm water or more at flow rates of 5 ml/h or more.

Figure 6H:
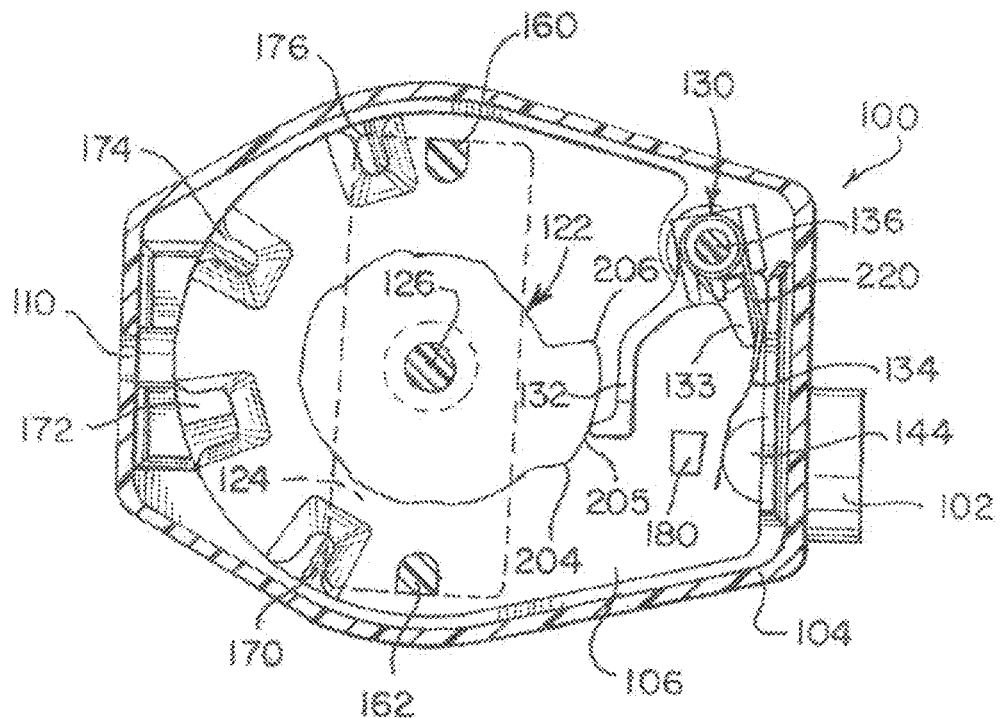

The final setting, FIG. 6H, of approximately at least 400 mm water (3,920 Pa) minimizes flow as a "virtual off" setting, that is, as substantially closed. This final setting is achieved by exposing cam follower 132 to outermost cam surface 205, defined by points 204 and 206, having greatest radial distance 218. This greatest cam setting forces stiffener element 133 of spring arm unit 130 against valve spring 134 to shorten its active, effective length and thereby dramatically increase the biasing force applied against ball 144. The final opening pressure is increased by more than fifty percent over the prior setting. In other constructions, a stiffener element is forced against a valve spring during two or more final cam settings at desired pressure increments.

Spring arm unit 130 is shown in greater detail in FIGS. 9 and 9A with cam follower 132, stiffener element 133, and valve spring 134. Cam follower 132 terminates in a triangular head 233 with rounded or chamfered edges, one of which serves as a bearing surface 235. In a preferred construction, spring element 134 is formed from stainless steel having a thickness of 0.020 inches and terminates in an enlarged pad 230 for contacting the valve ball or other movable valve member. In one construction, spring element 134 is attached to the remainder of spring arm unit 130 by a post 232 and rivet 234 which are secured by ultrasonic welding. Torsion spring 220 has a first leg 221 which is retained in recess 236 of projection 238. Second spring leg 223 rests against an inner surface of the casing.

Use of torsion spring 220 is optional, and is possible because only spring element 134 contacts the movable valve member. As a result, additional spring force from torsion spring 220 can be utilized to force bearing surface 235 of cam follower 132 against a cam surface of the rotor. This biasing force provided by torsion spring 220 augments rotational position of the spring arm reflective of the intended cam displacement without otherwise impacting the force applied to the ball or other movable valve member. This provides for a more accurate and repeatable opening pressure and a more manufacturable and robust design as it reduces the need to maintain minimal friction such as when the valve spring element solely provides the force needed to maintain the cam follower on the cam surface.

The position of the components and features within adjustable valve unit 100 at the first pressure setting shown in FIG. 6A is illustrated at a deeper partial cross-sectional view in FIG. 7. Opening 222 into the lower cam portion of rotor 120 inhibits negative pressure from developing under rotor 120, that is, opening 222 ensures pressure equalization as cerebrospinal fluid passes through valve unit 100.

Figure 10:
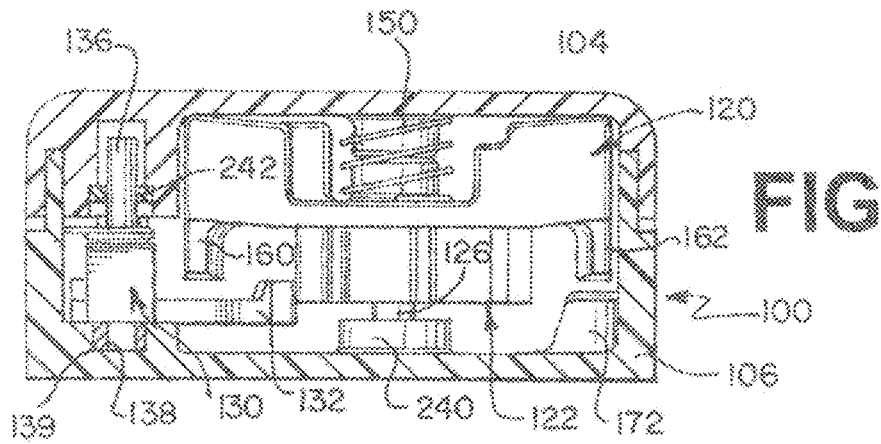
FIG. 10 is a side cross-sectional view of the adjustable valve unit of FIG. 8 along lines 10-10 showing axial lifting of the rotatable construct.

The transition from the first pressure setting to the second pressure setting is illustrated in FIGS. 8 & 10 as rotor 120 is translated upwardly by magnetic attraction with an adjustment tool so that rotor tooth 162 is able to clear casing lock stop 172. Cam follower 132 is shown in FIG. 8 at point 192 passing from first cam surface 191 to second cam surface 193. Lower cam section 122 has a sufficient height relative to cam follower bearing surface 235 to ensure that cam follower 132 remains in contact with a cam surface of cam portion 122 in both the constrained and unconstrained conditions. Rotor retention spring 150, FIG. 10, has been compressed, its biasing force being overcome by magnetic attraction between rotor 120 and the adjustment tool while it is positioned over valve unit 100. Also illustrated in FIG. 10 are upper and lower synthetic ruby bearings 242 and 139 for upper and lower axles 136 and 138, respectively, of spring arm unit 130. Synthetic ruby bearing 240 rotatably supports rotor axle 126.

Figure 11:
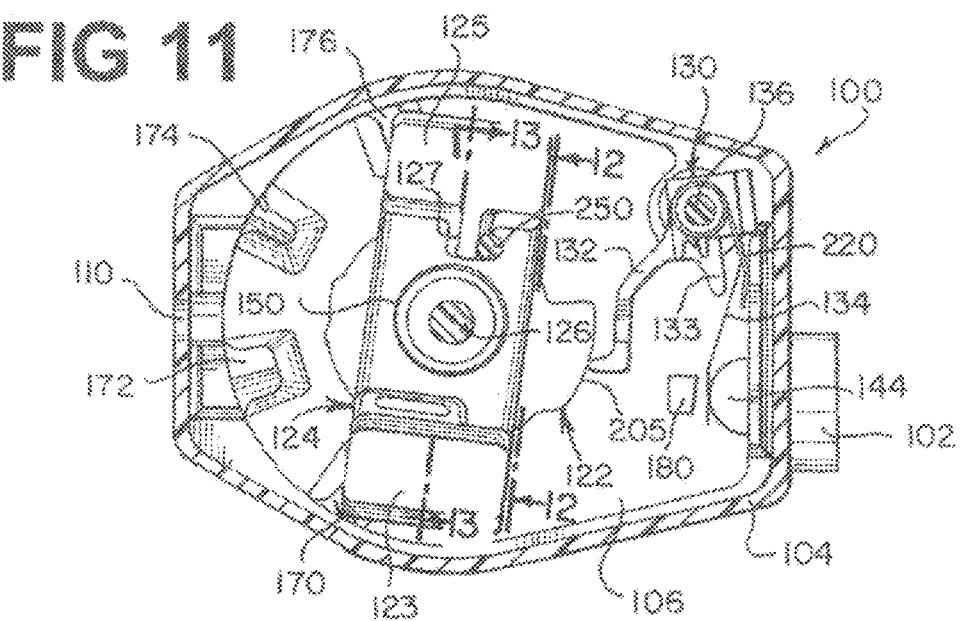
FIG. 11 is a shallower partial top cross-sectional view of the adjustable valve unit of FIG. 6H showing the "virtual off" position in an unconstrained condition.
Figure 12:
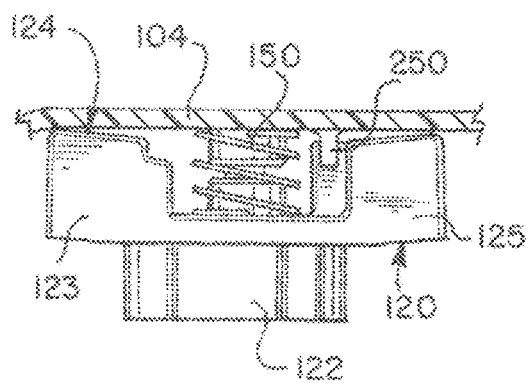
FIG. 12 is a side view along lines 12-12 of FIG. 11.

The position of the components and features within valve unit 100 at the final, "virtual off" or substantially closed setting shown in FIG. 6H is depicted at a shallower cross-sectional view in FIG. 11 in an unconstrained condition. Further clockwise rotation of rotor 120 is prevented by rotation stop or limiter 250 which projects downwardly from upper casing 104 to contact finger 127. Rotation stop 250 contacts the opposite surface of finger 127 when rotor 120 is turned fully counter-clockwise in an unconstrained condition. The actual position of rotation stop 250 may be shifted to the right of the position shown in FIG. 11 so that cam follower 132 is able to track nearly the entire portion of cam surface 205. Preferably, one side of stop 250 prevents rotor movement from the lowest setting directly to the highest setting, and also prevents the cam follower from touching the cam projection for the highest setting when the rotor is at its lowest setting. The other side of stop 250 prevents movement from the highest setting directly to the lowest setting. A side, partial cross-sectional view of rotation stop 250 blocking rotor housing 124, as well as spring 150 compressed between rotor 120 and upper casing 104, is shown in FIG. 12 for this unconstrained condition.

Figure 13:
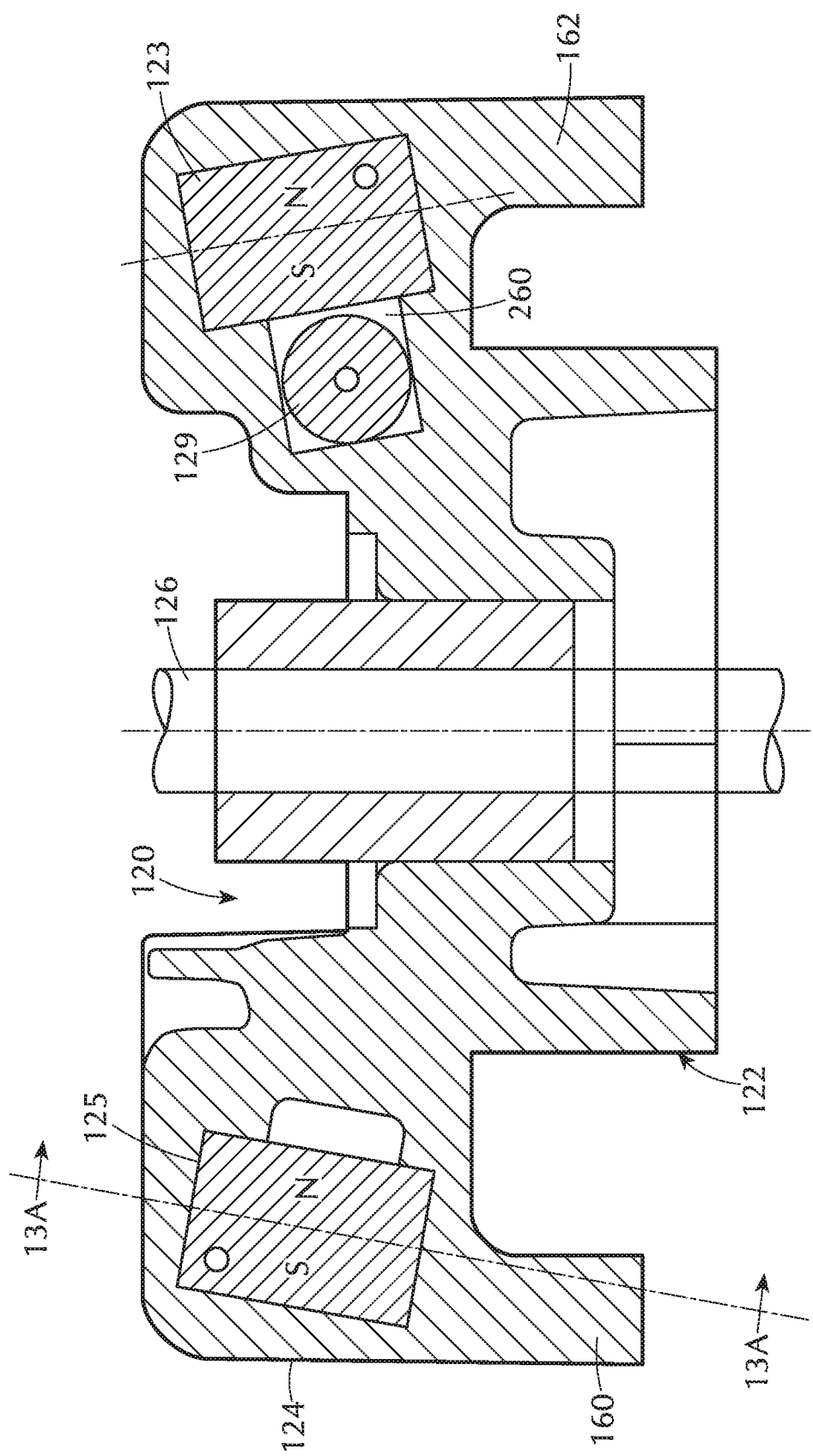
FIG. 13 is a side cross-sectional view along lines 13-13 of FIG. 11.

Further detailed views of selected features and components of rotor 120 in one construction are illustrated in FIGS. 13 & 13A. In particular, the housing portion 124 is shown as integral with cam portion 122, similar to monolithic rotor 120a of FIG. 1A. Pocket cavity 260, FIG. 13, contains magnet 123 and tantalum reference ball 129 which is readily visible during imaging of the valve unit 100 after implantation in a patient to confirm the actual pressure setting. Pocket cavity 262 holds magnet 125. A partial end view of housing portion 124 through magnet 125, pocket 262 and rotor tooth 160 is provided in FIG. 13A.

It is therefore the particular design of the abutting rotor-tooth-to-lock-stop vertical surfaces requiring purely vertical lift by an adjustment tool to overcome the rotor-tooth-to-lock-stop abutment in order to change the pressure setting that provides the resistance to change of valve settings even during exposure to external foreign magnetic fields. The rotor tooth-to-lock stop abutment mechanically prevents rotational movement from a given performance setting as the vertical surfaces provide no lead in to facilitate travel up and over the lock stops made of a sufficiently rigid material (such as a moldable plastic, for example, polyethersulfone (PES), polysulfone (PSU), polyphenylsulfone (PPSU)) and sufficient wall thickness (greater than 0.2 mm) to prevent flexure. Axial movement is restricted due to the orientation of the rotating construct magnets inducing a combined attraction and repulsion when interacting with a strong north or south magnet. Furthermore, the interference between the axle and the bushing surface of the rotating construct mechanically limit tilt associated with attraction/repulsion to an external magnetic field.

However, it is only when the downward projecting rotor teeth 160, 162 of the rotor housing 124 are properly locked, engaged or seated in corresponding setting pockets 171, 171', 171", 171''' defined by at least one of the lock stops 170, 172, 174, 176 projecting upwardly from the lower casing 106 that the programmable implantable bodily fluid drainage valve is resistant to magnetic fields. It is mechanically possible for the downward projecting teeth 160, 162 when vertically lowered to undesirably rest on the lock stops 170, 172, 174, 176, as depicted in FIG. 8 wherein rotor tooth 162 is resting on lock stop 172. When the rotor teeth 160, 162 are resting on the lock stops 170, 172, 174, 176 (i.e., not properly seated in the respective setting pockets defined by the lock stops) the programmable implantable bodily fluid drainage valve is at risk of possible unwanted change to the valve setting when exposed to magnetic fields such as during an MRI procedure. Heretofore, conventional programming valves are not able to verify whether the rotor teeth 160, 162 are properly seated in the setting pockets 171, 171', 171", 171'''. Experimental testing has confirmed that the valve setting remains unchanged when subject to magnetic fields up to approximately 3 T if the rotor teeth are properly locked, engaged or seated in the respective setting pockets. To be certain, prior to being exposed to a magnetic field (e.g., prior to undergoing an MRI procedure, the programmed valve setting must once again be verified by medical personnel using the indicator tool from the associated toolset or alternatively the medical personnel would have to use a tool to confirm proper engagement. The possibility of a change in valve setting if the rotor teeth are not properly seated in a setting pocket during exposure to magnetic fields, despite its relative small probability of occurrence, is still particularly problematic since the implantable programmable bodily fluid drainage valve cannot be guaranteed as being resistant to magnetic fields in such circumstances.

The present inventive improved implantable valve drainage system eliminates this uncertainty by verifying whether the downward projecting rotor teeth 160, 162 are properly seated in the respective seating pockets 171, 171', 171", 171''', that is, confirm whether the magnetic field resistance mechanism is properly engaged to carry out its intended functionality.

Figure 6I:
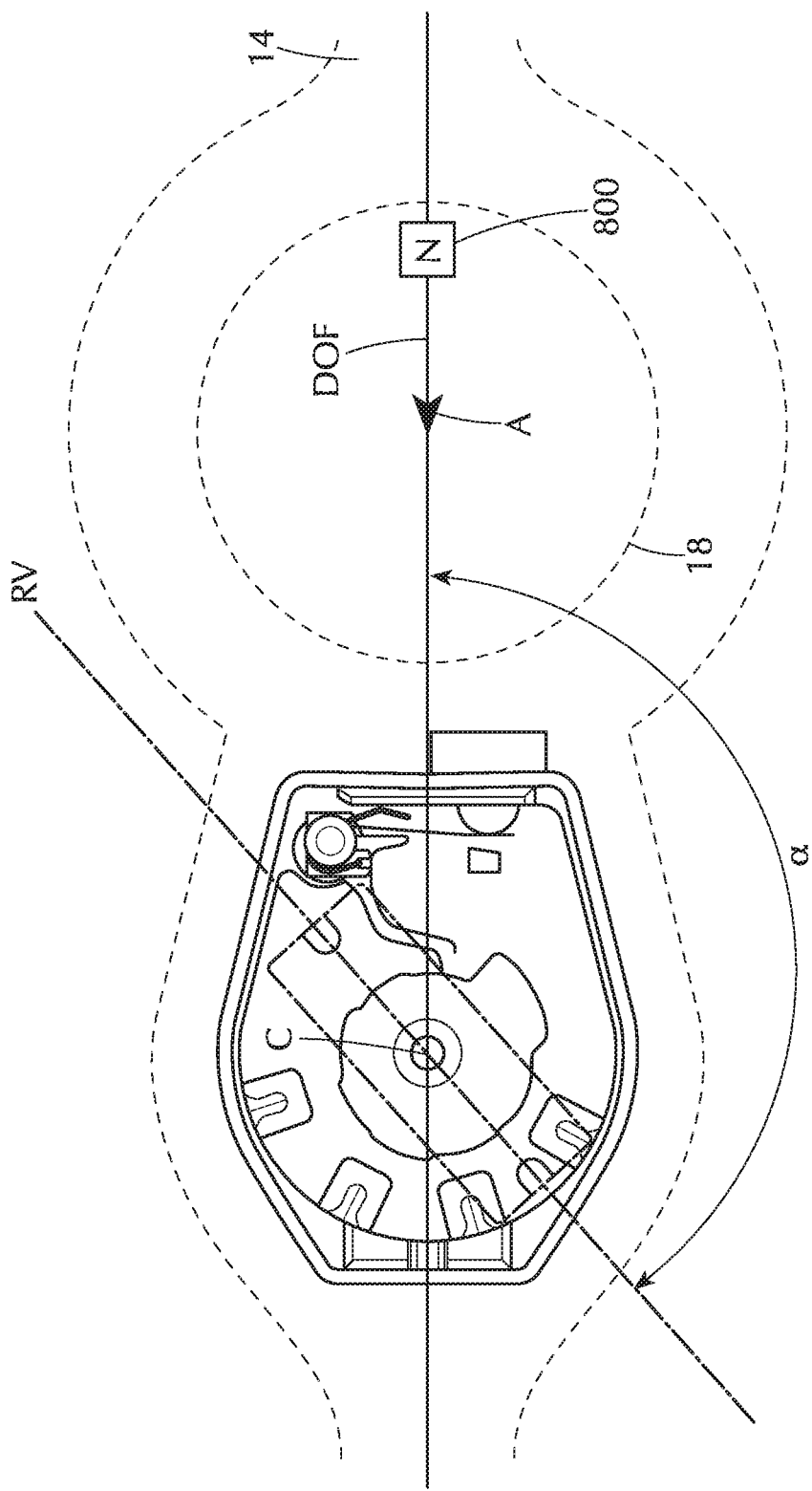
FIG. 6I is a partial cross-sectional view of the adjustable valve unit of FIG. 4 at an exemplary first pressure setting illustrating the arrow marking on the programmable valve device denoting a direction of fluid flow therethrough and the fixed reference magnet.
Figure 6J:
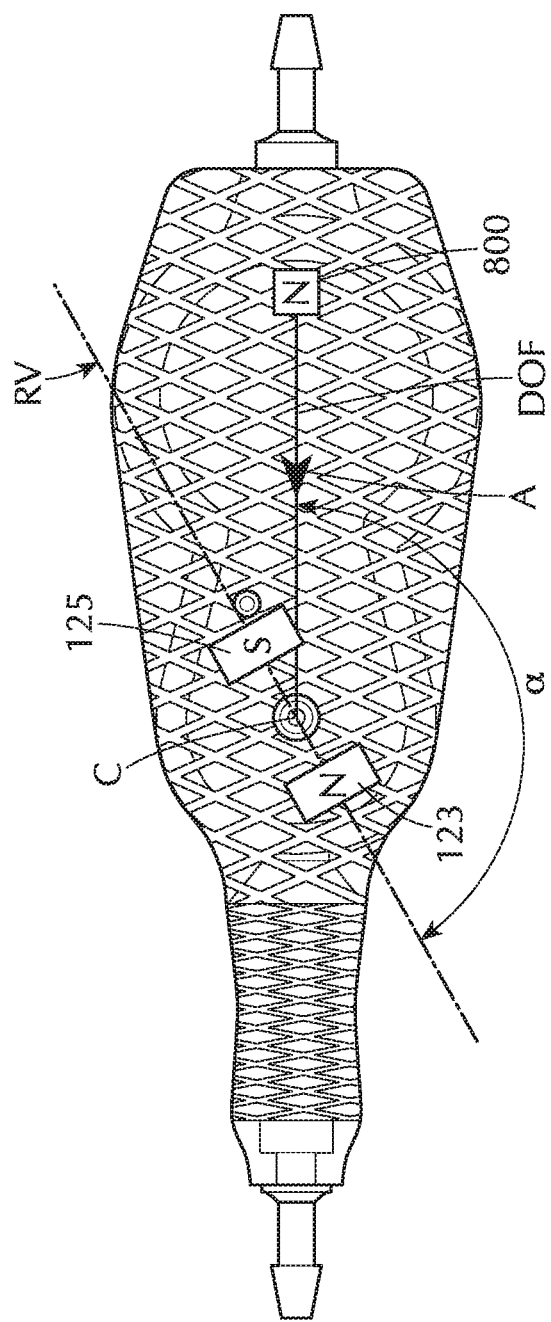
FIG. 6J is a top view of the programmable valve device of FIG. 1 wherein the adjustable valve unit is at the same first pressure setting illustrated in FIG. 6I and also showing the direction of flow arrow marking and positioning of the fixed reference magnet.
Figure 14:
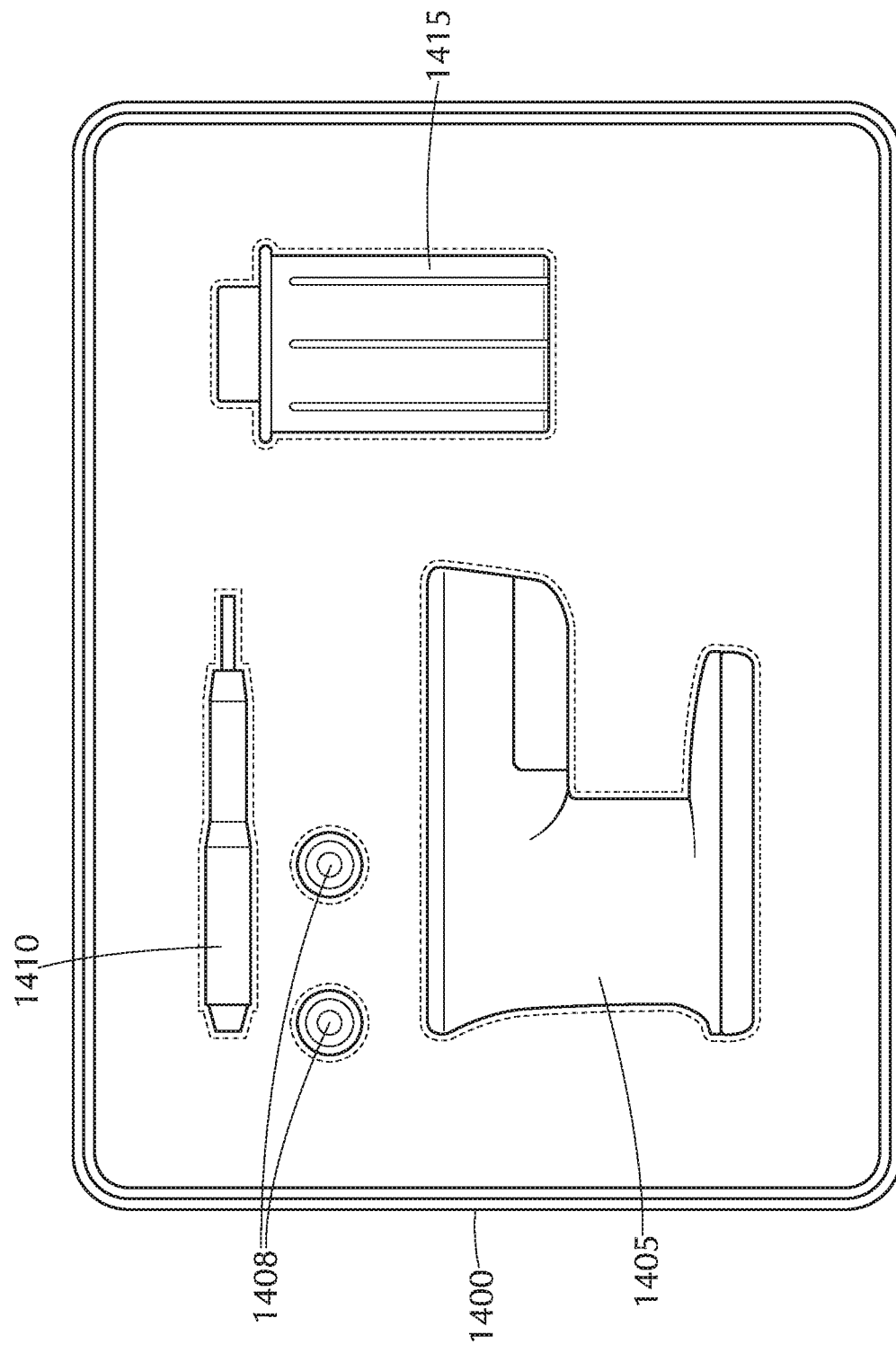
FIG. 14 is a perspective view of a tool set including an integrated locator/indicator tool, an adjustment tool and a screwdriver.

This is realized by configuring the programmable shunt valve 10 to include a fixed reference magnet 800, in addition to the primary magnetic elements 123, 125 disposed in the housing 124 of the rotor 120 of the adjustable valve unit, as illustrated in FIG. 6I. Referring to FIG. 6J, preferably, the fixed reference magnet 800 is located between the proximal connector 14 and the sampling/pumping chamber 18 within the direction of flow of the shunt valve. Preferably, fixed reference magnet 800 has a different magnetic strength from the primary magnetic elements 123, 125 and a different nominal distance between magnets (i.e., distance between reference magnet 800 and primary magnet 123 compared to distance between primary magnets 123 and 125) for proper identification. Nominal distance between primary magnetic elements 123, 125 is approximately 5.48 mm as measured from bottom inner corner to bottom inner corner. Fixed reference magnet 800 nominal distance is 17.5 mm from RC axle to leading edge of reference magnet 800. The fixed reference magnet 800 is aligned with an arrow indicia or marking "A" on the programmable shunt valve 10 itself denoting the direction of flow of fluid therethrough and a center point "C" midway between the magnetic elements 123, 125. A line passing through these three points (referred to as a direction of flow line) is the basis for determining the orientation of the programmable shunt valve 10 using an integrated locator/indicator tool 1405 from the exemplary tool set 1400 in a case, as illustrated in FIG. 14. Also included in the tool set is an adjustment tool 1415, a screwdriver 1410 and spare batteries 1408. It is noted that the locator and indicator tools described herein and illustrated in the accompanying drawings have been integrated into a single device for simplicity of operation. It is, however, contemplated and within the intended scope of the present invention for none, some, or all of the tools in the toolset to be integrated.

Figure 14A:
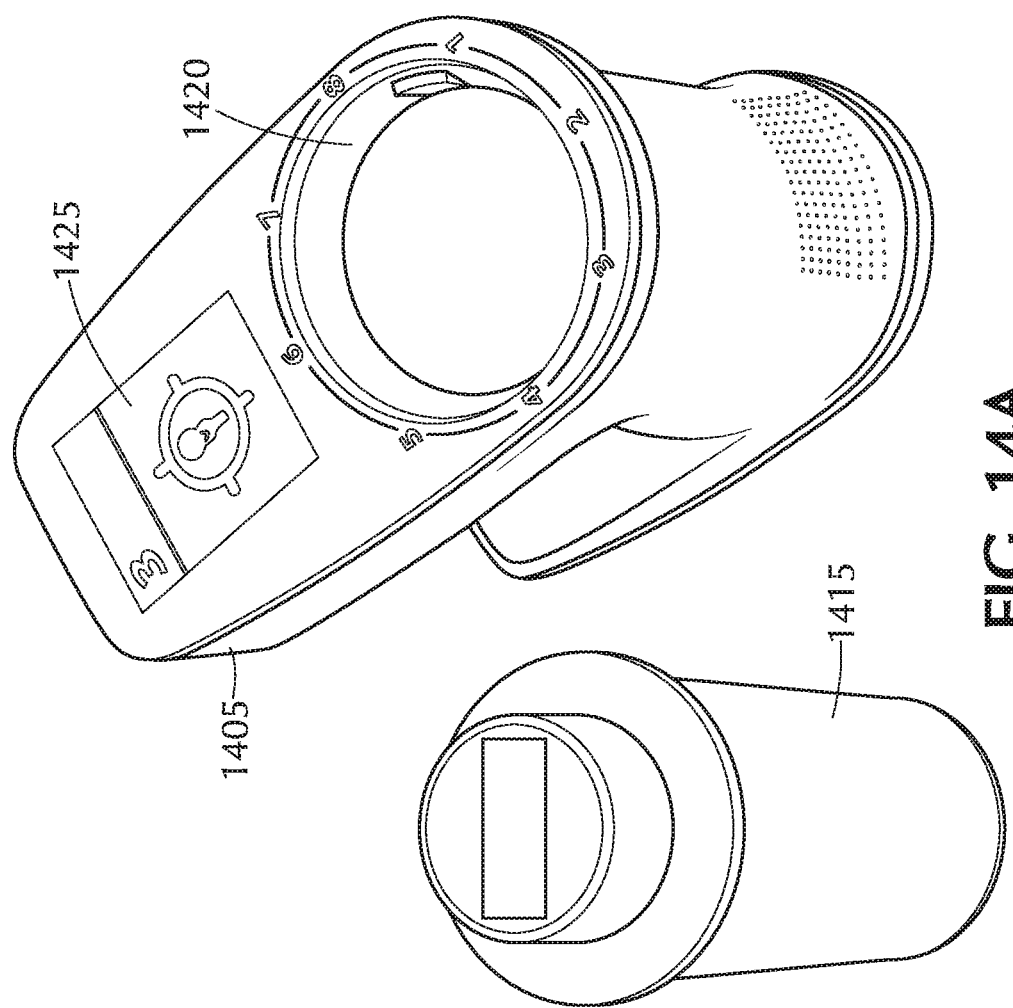
FIG. 14A is a top perspective view of the integrated locator/indicator tool and adjustment tool of FIG. 14, prior to the adjustment tool being inserted into the integrated locator/indicator tool.
Figure 14B:
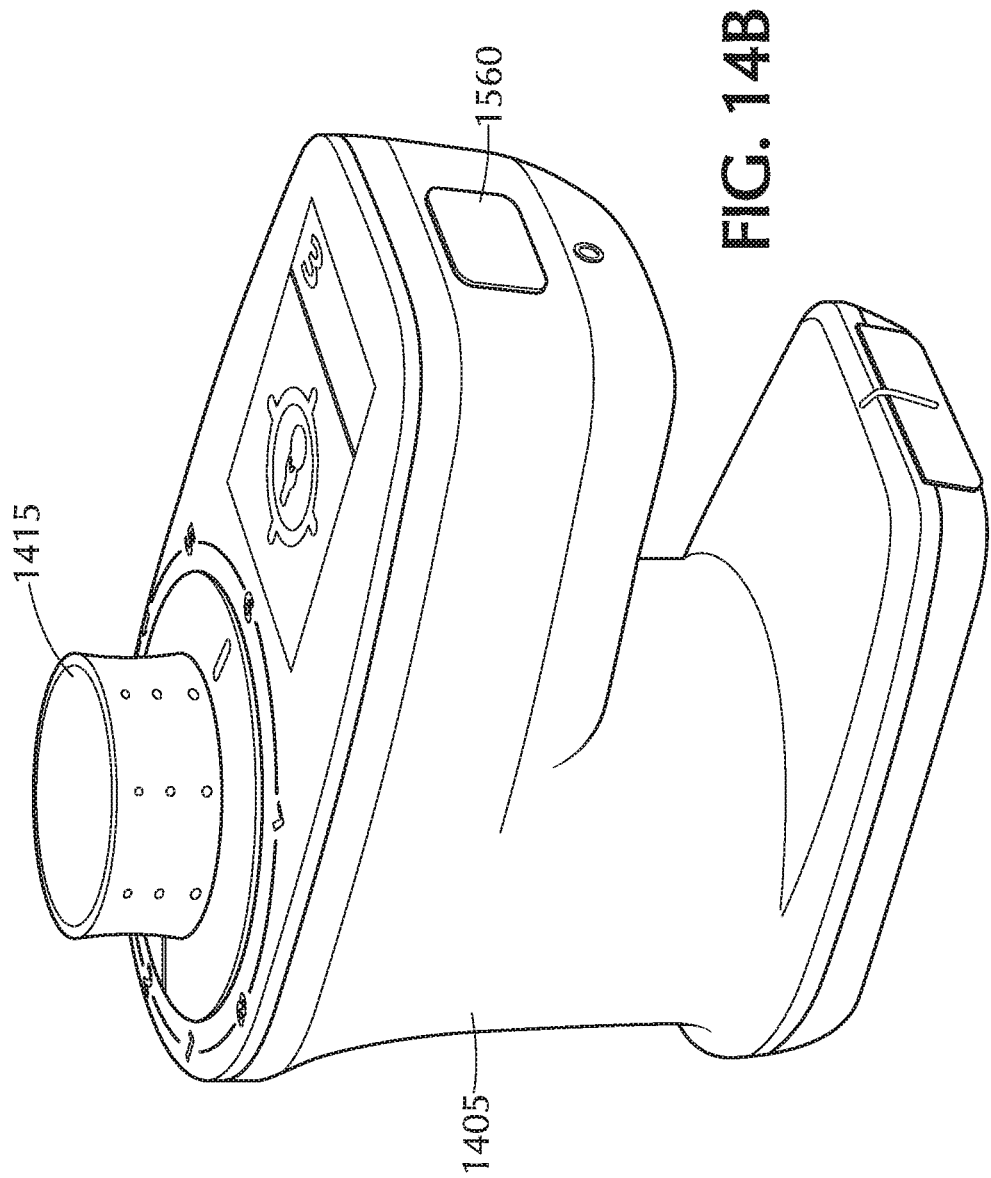
FIG. 14B is a top perspective view of the integrated locator/indicator tool and adjustment tool of FIG. 14, with the adjustment tool inserted into a complementary cavity in the integrated locator/indicator tool.

A top perspective view of the integrated locator/indicator tool 1405 and adjustment tool 1415 of FIG. 14, prior to the adjustment tool 1415 being inserted into a cavity 1420 of the integrated locator/indicator tool 1405, is shown in FIG. 14A. While FIG. 14B shows the adjustment tool 1415 following insertion into the cavity 1420.

Figure 15:
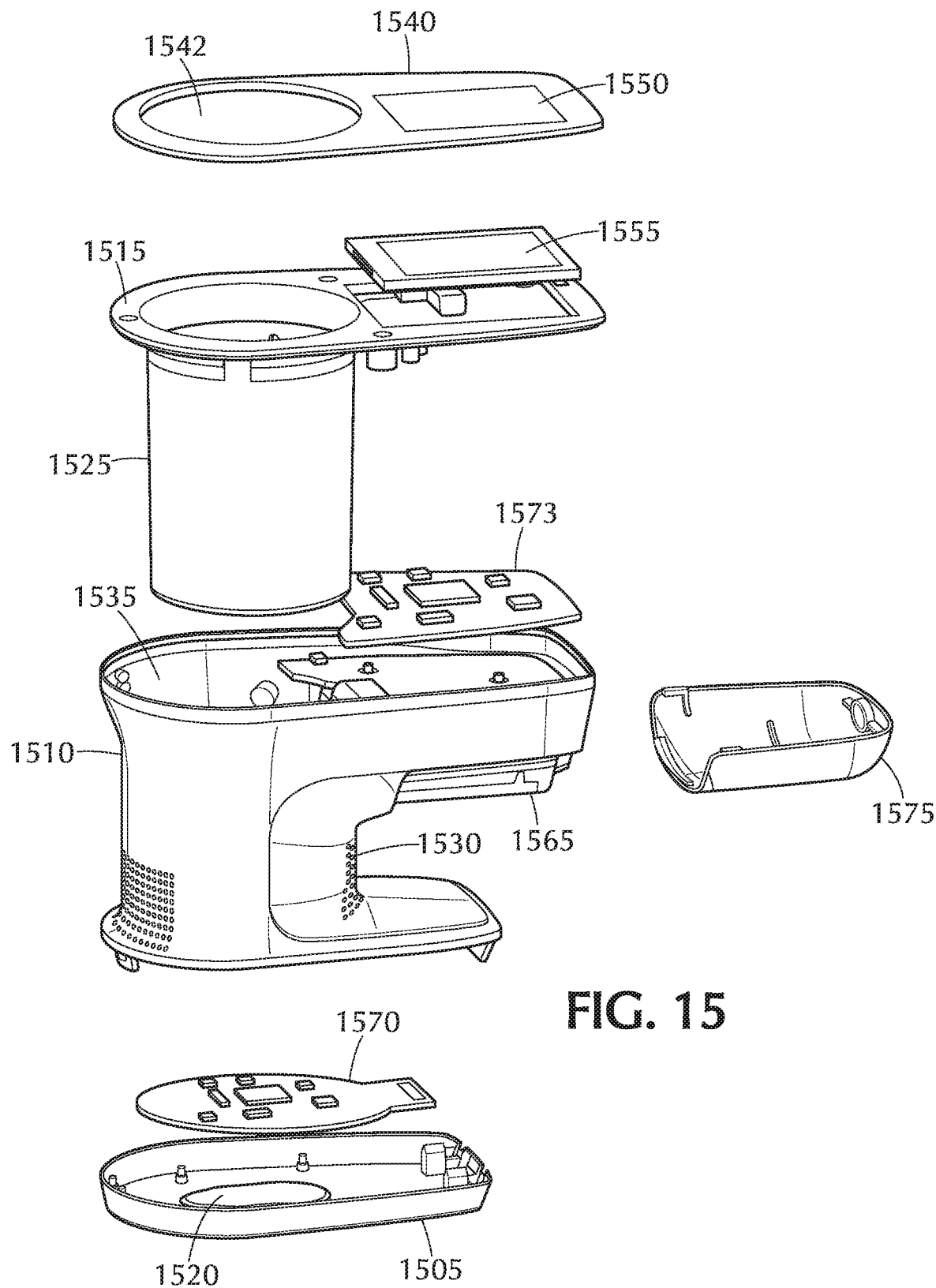
FIG. 15 is an exploded perspective view of the integrated locator/indicator tool of FIG. 14.

FIG. 15 is an exploded perspective view of the integrated locator/indicator tool 1405 of FIG. 14 which includes a housing 1500. In the illustrated example, housing 1500 comprises a bottom housing section 1505, a middle housing section 1510 and a top housing section 1515, each separate from one another. A cylindrical shaped section 1530 of the middle housing section 1510 defines a passageway or channel 1535 extending longitudinally therethrough. Top housing section 1515 has a chimney 1525 complementary in size and shape to be received within the passageway or channel 1535 of the cylindrical shaped section 1530 of the middle housing section 1510. Chimney 1525 is closed at one end and open at an opposite end. The open end of the chimney 1525 receiving therein the adjustment tool 1415, as described in detail below. An exterior surface of the bottom housing section 1505 has a recess 1520 defined therein that is complementary in shape and size to the outer contour of the programmable implantable bodily fluid drainage valve. In use, the integrated location/indication tool 1405 is positioned with the exterior surface of the bottom housing section 1505 against the skin of the patient and the implantable bodily fluid drainage valve seated within the recess 1520. A top covering or layer 1540 may be mounted to the top of the assembled housing. Such covering or layer 1540 has a complementary size and shape opening 1542 to that of the chimney 1525. Disposed about the perimeter of the opening 1542 are a series of markings representing the different valve settings in predetermined increments (e.g., 1, 2, 3, 6, 7, 8). A second opening 1550 in the top covering or layer 1540 permits viewing therethrough of a display 1555, such as a Liquid Crystal Display (LCD). The integrated locator/indicator tool 1405 is powered by one or more batteries and turned ON/OFF by a button 1560. The batteries are housed within a battery enclosure assembly 1565 that includes a tray with electronic contact terminals between which the batteries are inserted. Access to the battery enclosure assembly 1565 for insertion/removal of the batteries therefrom is via a removeable battery door assembly 1575. A two-dimensional array of 3-axis magneto-resistive sensors 1570 printed on a circuit board detects the magnetic field pattern produced by the magnetic elements 123, 125 disposed in the housing 124 of the rotor 120 and the fixed reference magnet 800. It is within the intended scope of the present invention to substitute other types of sensor arrays capable of detecting magnetic fields, such as Hall sensors, for the 3-axis magneto-resistive sensors 1570. Another printed circuit board 1573 includes a processor/controller and memory device.

Figure 16:
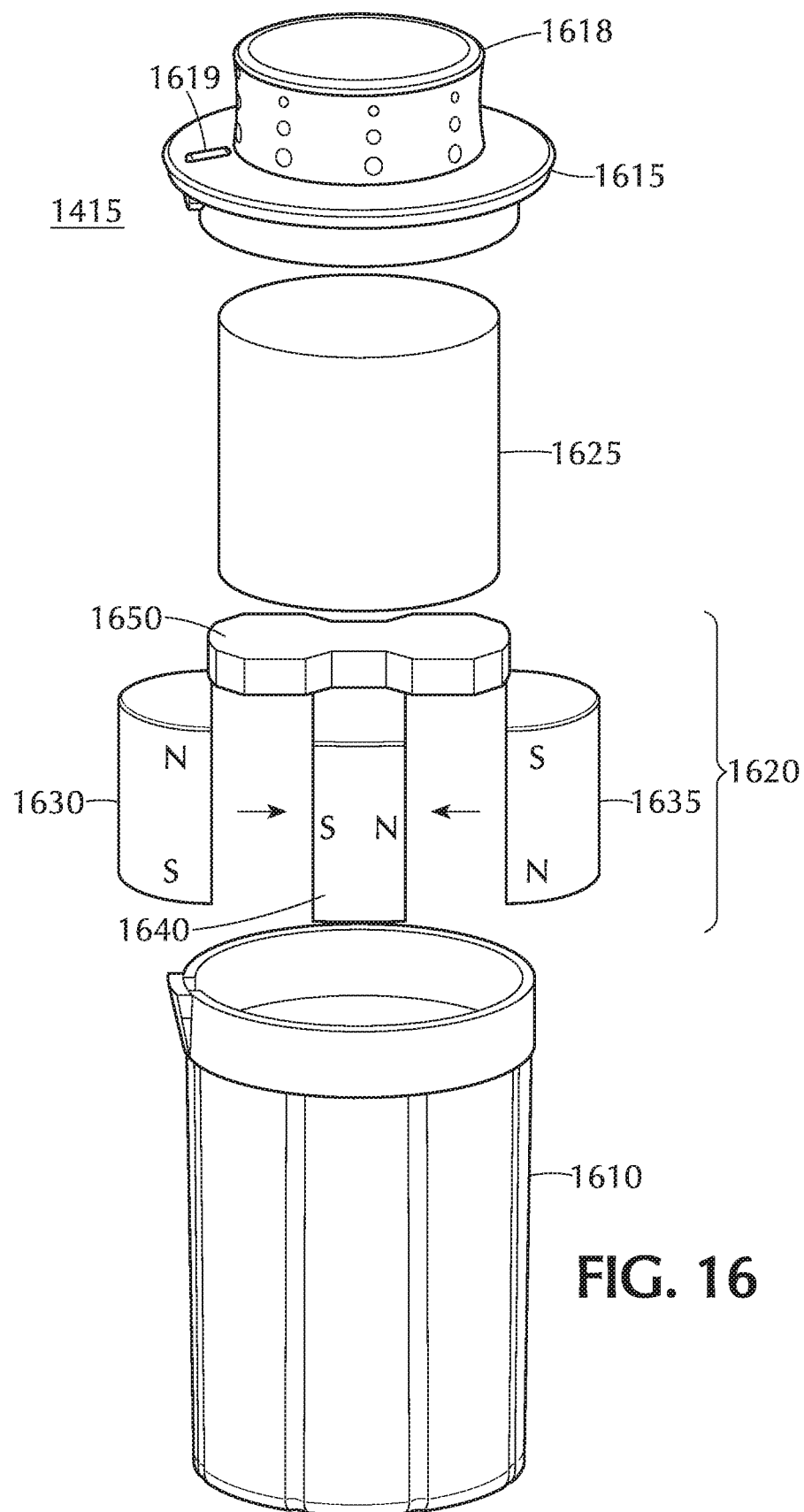
FIG. 16 is an exploded perspective view of the adjustment tool of FIG. 14.
Figure 16A:
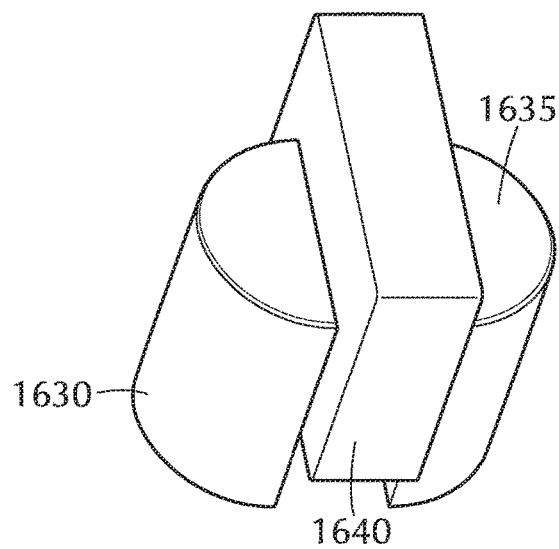
FIG. 16A is a perspective view of the placement of the half round magnets on either side of the magnet shield comprising part of the magnet assembly of FIG. 16.
Figure 16B:
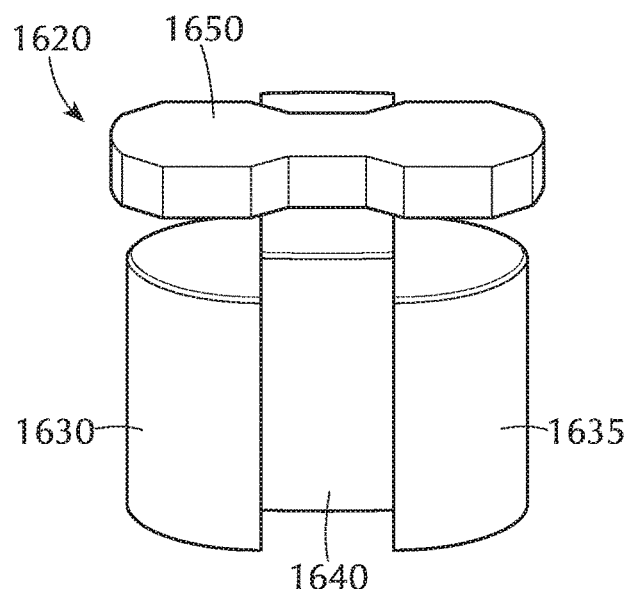
FIG. 16B is a perspective view of the assembled magnet assembly of FIG. 16.
Figure 16C:
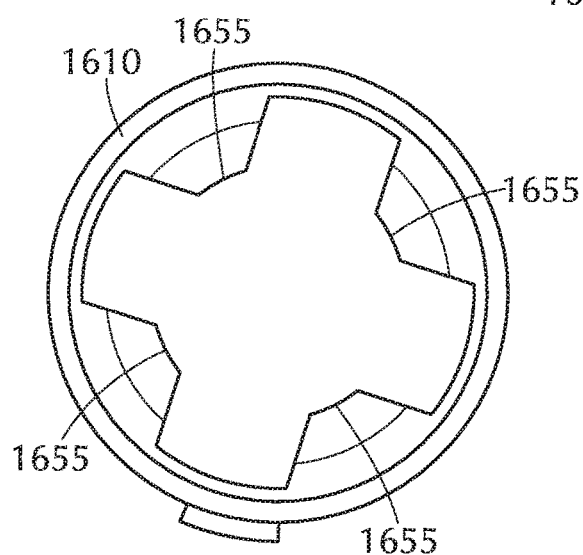
FIG. 16C is a top view of the assembled bottom and middle housing sections of the adjustment tool of FIG. 16 showing the internal vertical ribs.
Figure 16D:
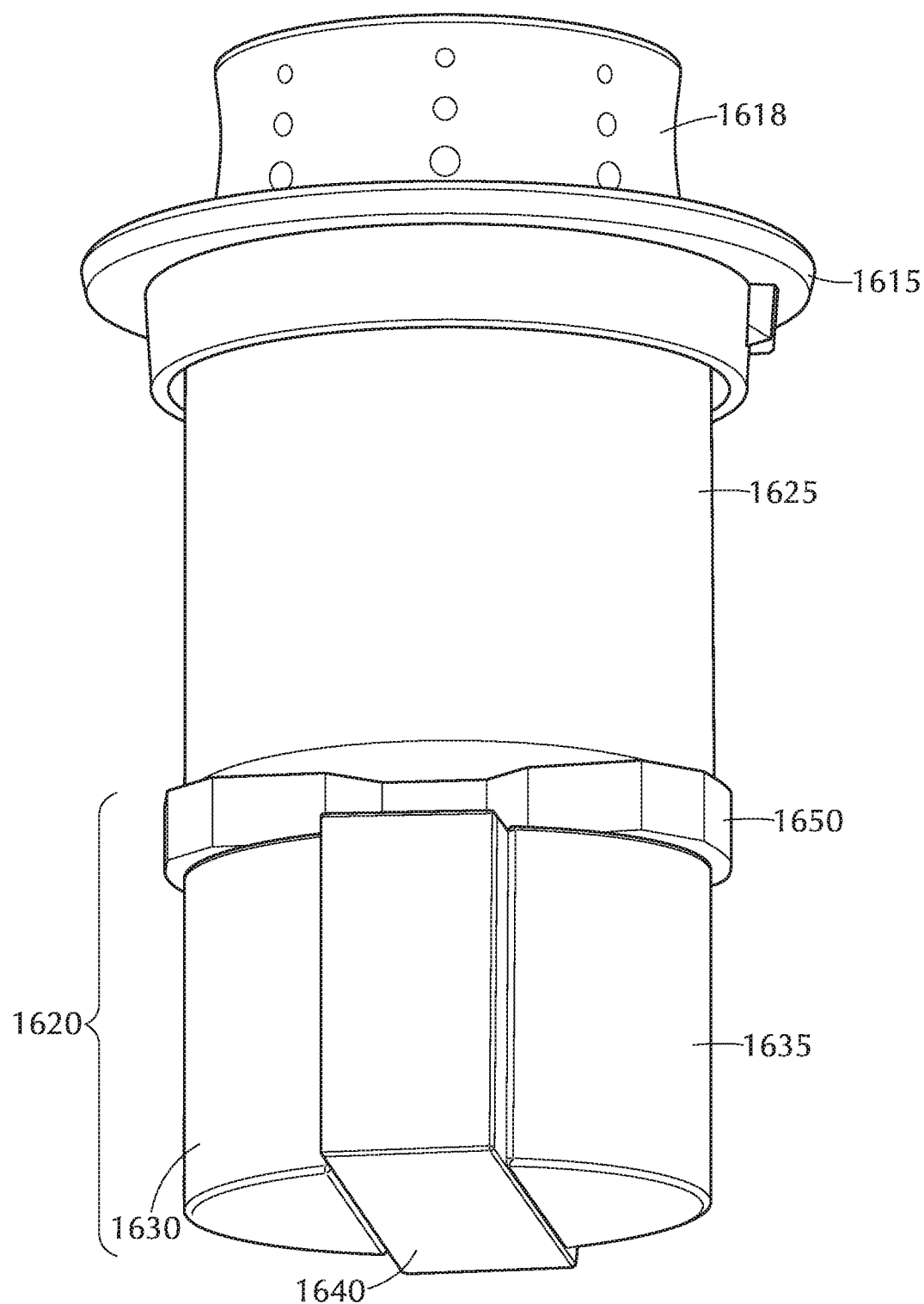
FIG. 16D is a perspective view of the assembled adjustment tool of FIG. 14 without the outer housing section to illustrate the magnet assembly.
Figure 17A:
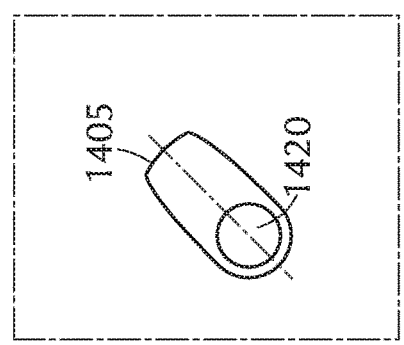
FIGS. 17A-17I are sequential illustrations of the steps for operating the electronic toolset in accordance with the present invention.
Figure 17B:
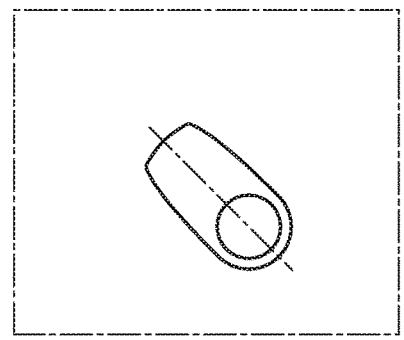
Figure 17C:
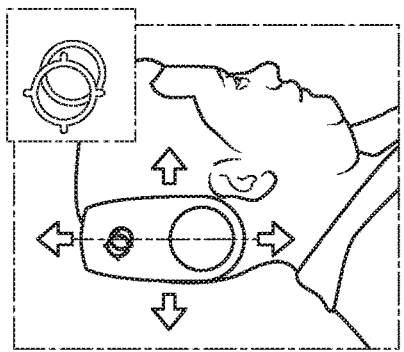
Figure 17D:
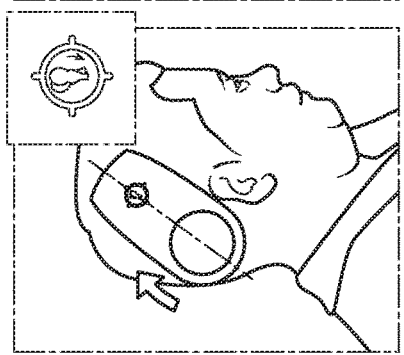
Figure 17E:
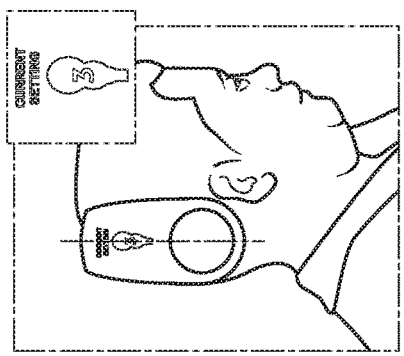
Figure 17F:
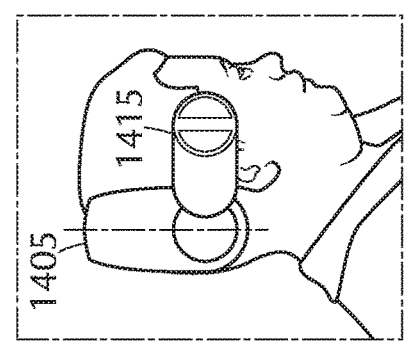
Figure 17G:
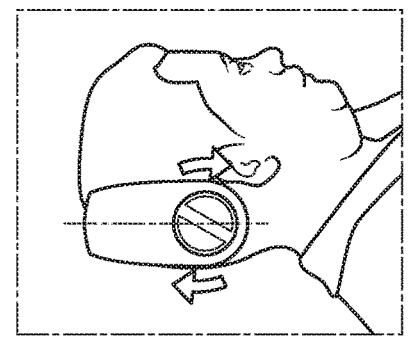
Figure 17H:
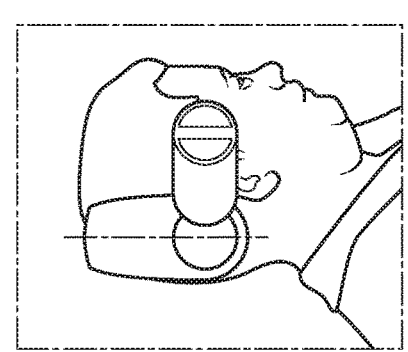
Figure 17I:
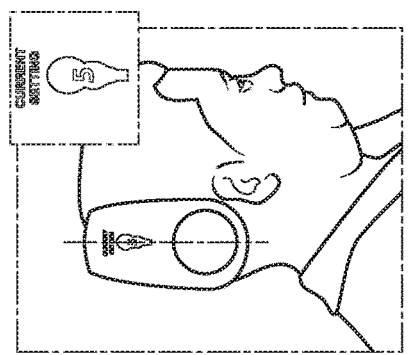

FIG. 16 is an exploded perspective view of the adjustment tool 1415 of FIG. 14. In the illustrated example, housing 1600 comprises an outer housing section 1610 and a top housing section 1615, each separate from one another. A magnet assembly 1620 is disposed in the outer housing section 1610. In particular, the magnet assembly 1620 in FIG. 16A is a Halbach array comprising two half round magnets 1630, 1635 connected by a yoke 1650 and separated by a shield magnet 1640 that redirects the magnetic field allowing deeper penetration. The strength of the half round magnets 1630, 1635 selected for use in the adjustment tool 1415 depends on one or more factors, such as distance from the valve and the design of the sensor array. In the magnet assembly 1620, the two half round magnets 1630, 1635 are rotated until their flat side lays flush against the shield magnet 1640, as depicted in FIG. 16A. The orientation of the magnets 1640, 1630, 1635 should preferably be as shown in FIG. 16 with the magnet north side of the shield magnet 1640 in contact with the half round magnet 1630, 1635 with a magnetic north pointed toward the bottom of the outer housing section 1610. One of the two half round magnets 1630, 1635 faces the tantalum reference ball 129 (FIG. 13). The shield magnet 1640 is partially repelled by the half round magnets 130, 1635 and thus is held down by a yoke 1650 mounted on top of the shield magnet 1640 that, when assembled, is also in contact with the two half round magnets 1630, 1635. It is these components of the magnet assembly 1620 that when assembled together are inserted into the outer housing section 1610 so that the two half round magnets 1630, 1635 are received in respective recesses 1655 defined in an interior surface of the outer housing section 1610 with the half round magnet facing the tantalum ball 129 facing towards the '1 to 8 stop'. As is visible in the top view in FIG. 16C, the outer housing section 1610 includes a plurality of vertical ribs 1655 with which the half round magnets 1630, 1635 connect. A cylindrical shaped spacer 1625 is positioned above the yoke 1650 (FIG. 16D). The top housing section 1615 with a marking indicator is secured to the outer housing section 1610 forming the assembled adjustment tool 1415.

The magnetic field pattern produced by the magnetic elements 123, 125 disposed in the housing 124 of the rotor 120 and the fixed reference magnet 800 is detected by the two-dimensional array of 3-axis magneto-resistive sensors 1570 of the integrated locator/indicator tool 1405. Once these three magnets are detected, the center point "C" midway between the two detected magnetic elements 123, 125 is located. The detected fixed reference magnet 800 is connected with the arrow indicia or marking "A" denoting the direction of flow on the implantable valve and the center point "C" midway between the two detected magnetic elements 123, 125 to define a direction flow line as a reference line for aligning the integrated locator/indicator tool 1405 with the direction of flow line on the valve. Once the user has centered and oriented the toolset over the valve mechanism the toolset will provide an indication of valve setting based on the angle of north/south poles and facilitate adjustment of the valve setting.

FIGS. 18A-18I are sequential steps in operation of the improved electronic toolset of FIG. 14 in accordance with the present invention. In FIG. 18A the integrated locator/indictor tool 1405 is powered on by pressing the power button 1560. Holding the power button 1560 for a predetermined period of time, e.g., approximately 3 seconds, calibrates, clears or zeros out the integrated locator/indicator tool 1405, as illustrated in FIG. 18B. Then a bottom surface (sensor floor) of the integrated locator/indicator tool 1405 is positioned against the skin above the implantable valve system such that the implantable valve is received in the complementary size and shaped recess 1520 defined in the exterior surface of the bottom housing section 1505, as illustrated in FIG. 18C. The integrated location/indication tool 1405 is moved in the appropriate direction (as indicated by the four arrows pointing in different directions) until the two circular visual images viewed on the LCD display 1555 are aligned with one another, indicating that the center of the adjustable valve unit 100 has been aligned with the center of the adjustable valve unit 100. Having centered the locator/indictor tool 1405 above the adjustable valve unit 100, then in FIG. 18D, the integrated locator/indicator tool 1405 is rotated until the two visual icons (complementary in shape (key hole shaped) to the implantable valve) displayed within the two circular visual images are aligned with one another to orient the integrated location/indication tool 1405 in the proper direction of flow of the implantable valve. It is now that the integrated location/indication tool 1405 has been centered and oriented in a direction of flow of the implantable valve, that the current indication or valve setting is read and visually displayed on the LCD (FIG. 18E). If the current valve setting is to be changed or programmed to a new valve setting, then in FIG. 18F the adjustment tool 1415 is inserted into the cavity 1420 of the integrated location/indication tool 1405 and rotated until the reference marking 1619 on the adjustment tool 1415 is aligned with the marking on the top lens 1540 corresponding to the read current valve setting. In FIG. 18G the adjustment tool 1415 is rotated clockwise/counterclockwise to the marking on the top lens corresponding to the new valve setting. Once set to the new valve setting, in FIG. 18H the adjustment tool 1415 is removed from the integrated locator/indicator tool 1405 (while the integrated location/indication tool 1405 remains stationary in place) and this new valve setting is now automatically detected by the integrated location/indication tool 1405 and visibly displayed on the LCD 1555 (FIG. 18I). It is noted that the positioning of the integrated location/indication tool 1405 remains unchanged in steps 18E-18I. The improved electronic toolset eliminates the requirement or need to have to once again locate the center of the valve and then confirm the new valve setting following adjustment by the adjustment tool 1415.

The present inventive electronic toolset, as illustrated in FIG. 14, is suitable for use with a latest version or generation of the programmable implantable valve (FIG. 1) having a fixed reference magnet 800 separate from and in addition to the pair of primary magnets 123, 125 in the adjustable valve unit 100. As discussed above, the fixed reference magnet is used to determine the angular orientation of the valve. Other, possibly older, generations or versions of the programmable implantable valve not employing a reference magnet separate from and in addition to the pair of primary magnets in the adjustable valve unit, may still be in use. Then the angular orientation of the valve cannot be ascertained using the electronic toolset. Of course, a generation or version of the programmable implantable valve not employing a reference magnet may still be programmed using its corresponding older version or generation of toolset (i.e., one that is not adapted to detect the fixed reference magnet and based on such determine electronically the angle of orientation). However, this would require medical personnel to have available on site different versions or generations of electronic toolsets corresponding to whether the fixed reference magnet is present in the programmable implantable valve or not. Selecting the appropriate generation or version of toolset would first require the user to identify which version or generation of the implantable programmable valve was implanted. This may be accomplished via X-ray imaging (e.g., identifying the presence or absence of a reference magnet), however, such exposure has deleterious health effects and thus is to be avoided, whenever possible. Another drawback is that medical facilities would require an allocation of space for storing of the different versions or generations of toolsets. However, by far one of the most relevant risks is the possible selection and use by medical personnel of an incompatible generation or version of toolset with the implanted valve. These risks and drawbacks are reduced or overcome by using the present inventive universal electronic toolset that may be interchangeably used with both programmable implantable valves employing a fixed reference magnet as well as with earlier generations or versions of programmable implantable valves that do not include a fixed reference magnet.

Specifically, the present inventive locator/indicator tool 1405 includes circuitry for determining whether the fixed reference magnet 800 associated with the adjustable valve unit 100 is detected by the 2-dimensional array of 3-axis magneto-resistive sensors 1570. If the fixed reference magnet 800 is not detected (i.e., not present) the system classifies the magnets based on the historical valve mechanism and facilitates guidance for locating the valve but requires the user to determine orientation without electronic assistance or feedback, such as through palpation. Once the user has manually oriented the toolset over the valve mechanism the toolset will provide an indication of valve setting based on the angle of north/south poles and facilitate adjustment of the valve setting.

FIG. 18 is an exemplary flow chart of the specific steps taken to ascertain whether the implanted valve 10 is a generation or version that includes a fixed reference magnet 800 or not and associated operational steps taken in either case. Specifically, in step 2005 the presence of the fixed reference magnet 800 in the implanted valve 10 is ascertained using the two-dimensional array of 3-axis magneto-resistive sensors 1570 in the integrated locator/indicator tool 1405. If the fixed reference magnet 800 in the implanted valve 10 is detected in step 2010, then the center of adjustable valve unit 100 is located in step 2015. Specifically, locating the center of the adjustable valve unit 100 is achieved by first detecting the primary magnets 123, 125 associated with the adjustable valve unit 100 using the two-dimensional array of 3-axis magneto-resistive sensors 1570 in the integrated locator/indicator tool 1405. Once the primary magnets 123, 125 have been detected, the center of the adjustable valve unit 100 is located midway therebetween representing the center of the adjustable valve unit 100. Next, in step 2020 the direction of flow of the valve is determined based on the located center of the adjustable valve unit 100 (in step 2015) and the detected fixed reference magnet 800 (in step 2005). The integrated location/indication tool 1405 is moved until aligned with the identified center of the adjustable valve unit 100 and then the tool is rotated to the proper orientation aligned with the identified direction of flow of the valve. Preferably, this is accomplished visually on a display screen 1555 on which are displayed two separate icons (one fixed valve location icon illustrative of the implanted valve and one movable locator/indicator tool icon representing the integrated location/indication tool 1405). Note that a single icon can be used to denote more than one parameter (e.g., centering and direction of flow) hereinafter referred to as a "dual parameter icon." For example, the dual parameter icon may be an outer circle with a key-hole shape within the outer circle complementary to the outline of the programmable shunt valve device 10 in FIG. 1. In this exemplary dual parameter icon, the outer circle is representative of the centering parameter, whereas the key-hole shape within the outer circle denoting the direction of flow parameter. Integrated locator/indicator tool 1405 is moved and rotated appropriately until the two icons visible on the display screen 1555 are aligned relative to both the center (outer circles aligned) and direction of flow of the valve (key-hole shape). Now that the integrated location/indication tool 1405 is properly centered and the angle of orientation aligned with the direction of flow of the valve, the operation advances to step 2025 wherein the indication of the current valve setting is read by the integrated locator/indicator tool 1405 based on the angle of north/south poles of the primary magnets 123, 125 and facilitate adjustment of the valve setting, if desired.

If the new electronic toolset is being used with a previous generation or version of an implanted valve not employing a fixed reference magnet, then the presence of such fixed reference magnet will not be detected by the two-dimensional array of 3-axis magneto-resistive sensors 1570 in step 2010. The processing advances to step 2030 wherein the center of adjustable valve unit 100 is located in a manner similar to the processing discussed above with respect to step 2015. Specifically, locating the center of the adjustable valve unit 100 is achieved by first detecting the primary magnets 123, 125 associated with the adjustable valve unit 100 using the two-dimensional array of 3-axis magneto-resistive sensors 1570 in the integrated locator/indicator tool 1405. Once the primary magnets 123, 125 have been detected, the center of the adjustable valve unit 100 is located midway therebetween. The integrated location/indication tool 1405 is moved until aligned with the identified center of the adjustable valve unit 100. Once again this is preferably accomplished visually on the display screen 1555 on which are displayed two separate icons (one fixed valve location icon illustrative of the implanted valve and one movable locator/indicator tool icon representing the integrated location/indication tool 1405). When the presence of the fixed reference magnet is not detected, the icon displayed (e.g., the outer circle only) represents a single parameter (e.g., centering). There is no key-hole shape within the outer circle denoting the direction of flow parameter since such parameter is not detectable electronically with the assistance and feedback of the integrated locator/indicator tool 1405 in the absence of the fixed reference magnet 800. Integrated locator/indicator tool 1405 is moved appropriately until the two icons visible on the display screen 1555 are aligned relative to the center (outer circles aligned). Since no fixed reference magnet has been detected and thus no electronic assistance or feedback information regarding the direction of flow line of the implanted valve is provided by the integrated locator/indicator tool 1405, instead the operator is informed (via one or more senses such as visually, audibly and/or tactile) that the center and direction of flow, i.e., angle of orientation, of the adjustable valve unit must be determined manually without any electronic assistance or feedback information from any tool in the electronic toolset. Preferably, the user is guided step-by-step how to manually orient the toolset over the implanted valve, that is manually determine the center and direction of flow of the implanted valve (step 2035), without any electronic assistance or feedback information provided by the electronic toolset. By way of illustrative example based on the adjustable valve unit 100 configuration illustrated, the user may be instructed to palpate the area of interest until the adjustable valve unit 100 is located and then the center is marked (i.e., the hard portion of the valve distal to the reservoir). The position of the inlet and outlet connector barbs on the respective catheters may also be determined through palpation and marked accordingly. A straight line passing through the three markings then represents the direction of flow line. Once the direction of flow line has been ascertained manually (without any electronic assistance or feedback information from any tool in the electronic toolset) the integrated locator/indicator tool 1405 is manually oriented to align with the direction of flow line. Now that the center of the adjustable valve unit 100 has been located and the integrated location/indication tool 1405 has been manually aligned with the manually detected orientation of the direction of flow of the implanted valve, the operation advances to step 2040 wherein the indication of the current valve setting is read by the integrated locator/indicator tool 1405 based on the angle of north/south poles of the primary magnets 123, 125 and facilitate adjustment of the valve setting, if desired. As previously mentioned, with other valve configurations the steps for locating the center and direction of flow of the valve may vary from those described above using other fixed reference points on the valve.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for using a universal electronic toolset for indicating and adjusting of an implantable programmable bodily fluid drainage valve whether the implantable programmable bodily fluid drainage valve includes a fixed reference magnet used to determine an angle of orientation of the implantable programmable bodily fluid drainage valve or not, wherein the implantable programmable bodily fluid drainage valve includes an adjustable valve unit having a pair of primary magnetic elements, the method comprising the steps of:
   detecting using a magnetic field detection sensor array in an indicator tool of the electronic toolset whether the fixed reference magnet is present in the implantable programmable bodily fluid drainage valve;
   wherein if the presence of the fixed reference magnet in the implantable bodily fluid drainage valve is detected, further comprising the steps of:
   locating a center of the adjustable valve unit using the indicator tool of the electronic toolset;
   ascertaining a direction of flow of the adjustable valve unit based exclusively on electronic feedback provided by the indicator tool of the electronic toolset, without requiring manual physical palpation;
   aligning the indicator tool of the electronic toolset with the located center and the direction of flow of the adjustable valve unit;
   reading a current valve setting using the indicator tool of the electronic toolset;
   wherein if the presence of the fixed reference magnet in the implantable programmable bodily fluid drainage valve is not detected, further comprising the steps of:
   locating the center of the adjustable valve unit using the indicator tool of the electronic toolset;
   establishing the direction of flow of the adjustable valve unit exclusively by manual physical palpation, without electronic feedback from the indicator tool of the electronic toolset;
   aligning the indicator tool of the electronic toolset with the located center and the direction of flow of the adjustable valve unit;
   reading the current valve setting using the indicator tool of the electronic toolset.

2. The method according to claim 1, wherein each of the locating steps comprises the steps of:
   detecting using the magnetic field detection sensor array a magnetic field pattern produced by each of the pair of primary magnetic elements; and
   finding a midway point between the detected pair of primary magnetic elements representing the center of the adjustable valve unit.

3. The method according to claim 2, wherein the direction of flow of the adjustable valve unit in the ascertaining step represents a reference line intersecting with: (i) an indicia denoting direction of flow of fluid through the implantable bodily fluid drainage valve; (ii) the found midway point between the detected pair of primary magnetic elements; and (iii) the detected fixed reference magnet.

4. The method according to claim 1, wherein the establishing step comprises the step of, exclusively via manually physically palpating an area of interest, locating the center and the direction of flow of the adjustable valve unit.

5. An implantable programmable bodily fluid drainage valve system comprising:
   an implantable programmable bodily fluid drainage valve having an adjustable valve unit including a pair of primary magnetic elements for programming the implantable programmable bodily fluid drainage valve to a desired valve setting;

a universal electronic toolset for indicating and adjusting the implantable programmable bodily fluid drainage valve; wherein the universal electronic toolset comprises:
an indicator tool having a magnetic field detection sensor array for: (i) detecting the pair of primary magnetic elements; and (ii) determining the presence or absence of a fixed reference magnet in the implantable programmable bodily fluid drainage valve;
circuitry for determining a center of the adjustable valve unit based on the detected pair of primary magnetic elements; the circuitry determining exclusively by electronic feedback from the universal electronic toolset an angular orientation of the implantable programmable bodily fluid drainage valve, when the fixed reference magnet is present; whereas the circuitry generating on a display of the implantable programmable bodily fluid drainage valve steps for determining exclusively by manual physical palpation the angular orientation of the implantable programmable bodily fluid drainage valve, when the fixed reference magnet is absent.

6. The system according to claim 5, wherein the angular orientation is a direction of flow of fluid through the implantable programmable bodily fluid drainage valve.

7. The system according to claim 5, wherein the circuitry determines the center of the adjustable valve unit by:
detecting using the magnetic field detection sensor array a magnetic field pattern produced by each of the pair of primary magnetic elements; and
finding a midway point between the detected pair of primary magnetic elements representing the center of the adjustable valve unit.

8. The system according to claim 7, wherein when the fixed reference magnet is detected as being present, the circuitry determines exclusively by the electronic feedback from the universal electronic toolset the angular orientation of the implantable programmable bodily fluid drainage valve representing a reference line intersecting with: (i) an indicia denoting direction of flow of fluid through the implantable bodily fluid drainage valve; (ii) the found midway point between the detected pair of primary magnetic elements; and (iii) the detected fixed reference magnet.

* * * * *